(12) United States Patent
Meyer et al.

(10) Patent No.: US 11,850,355 B2
(45) Date of Patent: Dec. 26, 2023

(54) SMART VALVED HOLDING CHAMBER

(71) Applicant: Trudell Medical International, London (CA)

(72) Inventors: Adam Meyer, London (CA); Bart Nowak, London (CA); Ronak Sakaria, London (CA); Heather Young, London (CA); Cameron Roadhouse, London (CA); Michael Lavdas, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 0 days.

(21) Appl. No.: 17/849,223

(22) Filed: Jun. 24, 2022

(65) Prior Publication Data

US 2023/0018347 A1    Jan. 19, 2023

Related U.S. Application Data

(63) Continuation of application No. 16/429,674, filed on Jun. 3, 2019, now Pat. No. 11,395,890.

(Continued)

(51) Int. Cl.
*A61M 15/00* (2006.01)
*A61M 16/20* (2006.01)
*A61M 16/00* (2006.01)

(52) U.S. Cl.
CPC ...... *A61M 15/0086* (2013.01); *A61M 15/009* (2013.01); *A61M 16/202* (2014.02);
(Continued)

(58) Field of Classification Search
CPC .......... A61M 15/0086; A61M 15/0088; A61M 15/009; A61M 16/202; A61M 2016/0024;
(Continued)

(56) References Cited

U.S. PATENT DOCUMENTS

| 4,984,158 | A | 1/1991 | Hillsman |
| 5,284,133 | A | 2/1994 | Burns et al. |

(Continued)

FOREIGN PATENT DOCUMENTS

| CA | 2415297 A1 | 1/2002 |
| CA | 2 607 458 A1 | 11/2006 |

(Continued)

OTHER PUBLICATIONS

Written Opinion of the International Searching Authority in International Application No. PCT/IB2017/052968 dated Sep. 5, 2017, 10 pages.

(Continued)

*Primary Examiner* — Elliot S Ruddie
(74) *Attorney, Agent, or Firm* — Crowell & Moring LLP

(57) ABSTRACT

A medication delivery system including a holding chamber having an input and an output end, a backpiece coupled to the input end of the holding chamber and having an electrical circuit and an opening. An MDI incudes an insert portion moveable between an engaged position wherein the insert portion is received in the opening and a disengaged position wherein the insert portion is removed from the opening, and at least one contact that completes the electrical circuit when the insert portion is in the engaged position.

16 Claims, 15 Drawing Sheets

Related U.S. Application Data

(60) Provisional application No. 62/680,232, filed on Jun. 4, 2018.

(52) U.S. Cl.
CPC ............ *A61M 2016/0024* (2013.01); *A61M 2016/0033* (2013.01); *A61M 2205/0272* (2013.01); *A61M 2205/331* (2013.01); *A61M 2205/3375* (2013.01); *A61M 2205/3584* (2013.01); *A61M 2205/3592* (2013.01); *A61M 2205/52* (2013.01)

(58) Field of Classification Search
CPC .. A61M 2016/0033; A61M 2205/0272; A61M 2205/331; A61M 2205/3375; A61M 2205/3584; A61M 2205/3592; A61M 2205/52; A61M 2016/0018; A61M 2205/18; A61M 2205/3306; A61M 2205/3553; A61M 2205/3561; A61M 2205/505; A61M 2205/581; A61M 2205/582; A61M 2205/583; A61M 2205/587; A61M 2205/6009; A61M 2205/6018; A61M 2205/6027; A61M 2205/702; A61B 2562/08; A61B 5/0022; A61B 5/0873; A61B 5/097; A61B 5/4839; A61B 5/7275; A61B 5/746; G16H 40/67; G16H 50/30
See application file for complete search history.

(56) References Cited

U.S. PATENT DOCUMENTS

| | | | |
|---|---|---|---|
| 5,331,953 | A | 7/1994 | Andersson et al. |
| 5,333,106 | A | 7/1994 | Lanpher et al. |
| 5,363,842 | A | 11/1994 | Mishelevich et al. |
| 5,431,154 | A | 7/1995 | Seigel et al. |
| 5,477,849 | A | 12/1995 | Fry |
| 5,505,192 | A | 4/1996 | Samiotes et al. |
| 5,505,195 | A | 4/1996 | Wolf et al. |
| 5,758,638 | A | 6/1998 | Kreamer |
| 5,794,612 | A | 8/1998 | Wachter et al. |
| 5,809,997 | A | 9/1998 | Wolf |
| 5,819,726 | A | 10/1998 | Rubsamen et al. |
| 5,865,172 | A | 2/1999 | Butler et al. |
| 5,937,852 | A | 8/1999 | Butler et al. |
| 6,073,628 | A | 6/2000 | Butler et al. |
| 6,138,669 | A | 10/2000 | Rocci, Jr. et al. |
| 6,148,815 | A | 11/2000 | Wolf |
| 6,192,876 | B1 | 2/2001 | Denyer et al. |
| 6,202,642 | B1* | 3/2001 | McKinnon ........ A61M 15/0083 128/200.14 |
| 6,230,704 | B1 | 5/2001 | Durkin et al. |
| 6,234,167 | B1 | 5/2001 | Cox et al. |
| 6,293,279 | B1 | 9/2001 | Schmidt et al. |
| 6,358,058 | B1 | 3/2002 | Strupat et al. |
| 6,578,571 | B1 | 6/2003 | Watt |
| 6,651,651 | B1 | 11/2003 | Bonney et al. |
| 6,823,862 | B2 | 11/2004 | McNaughton |
| 6,839,604 | B2 | 1/2005 | Godfrey et al. |
| 6,880,722 | B2 | 4/2005 | Anderson et al. |
| 6,904,907 | B2 | 6/2005 | Speldrich et al. |
| 6,932,083 | B2 | 8/2005 | Jones et al. |
| 6,934,220 | B1 | 8/2005 | Cruitt et al. |
| 6,958,691 | B1 | 10/2005 | Anderson et al. |
| 6,990,975 | B1 | 1/2006 | Jones et al. |
| 7,009,517 | B2 | 3/2006 | Wood |
| 7,072,738 | B2 | 7/2006 | Bonney et al. |
| 7,089,786 | B2 | 8/2006 | Walker |
| 7,091,864 | B2 | 8/2006 | Veitch et al. |
| 7,151,456 | B2 | 12/2006 | Godfrey |
| 7,159,533 | B1 | 1/2007 | Redd et al. |
| 7,191,777 | B2 | 3/2007 | Brand et al. |
| 7,198,172 | B2 | 4/2007 | Harvey et al. |
| 7,201,164 | B2 | 4/2007 | Grychowski et al. |
| 7,233,228 | B2 | 6/2007 | Lintell |
| 7,331,340 | B2 | 2/2008 | Barney |
| 7,383,837 | B2 | 6/2008 | Robertson et al. |
| 7,424,888 | B2 | 6/2008 | Harvey et al. |
| 7,495,546 | B2 | 2/2009 | Lintell |
| 7,597,099 | B2 | 10/2009 | Jones et al. |
| 7,661,423 | B2 | 2/2010 | Brand et al. |
| 7,730,847 | B1 | 6/2010 | Redd et al. |
| 7,748,382 | B2 | 7/2010 | Denyer et al. |
| 7,819,116 | B2 | 10/2010 | Brand et al. |
| 7,837,648 | B2 | 11/2010 | Blair et al. |
| 8,165,892 | B2 | 4/2012 | Carter et al. |
| 8,261,738 | B2 | 9/2012 | Denyer et al. |
| 8,342,172 | B2 | 1/2013 | Levy et al. |
| 8,403,861 | B2 | 3/2013 | Williams et al. |
| 8,424,517 | B2 | 4/2013 | Sutherland et al. |
| 8,464,707 | B2 | 6/2013 | Jongejan et al. |
| 8,474,448 | B2 | 7/2013 | Oi et al. |
| 8,550,067 | B2 | 10/2013 | Bruce et al. |
| 8,607,783 | B2 | 12/2013 | Takei et al. |
| 8,807,131 | B1 | 8/2014 | Tunnell et al. |
| 9,035,765 | B2 | 5/2015 | Engelhard et al. |
| 9,072,846 | B2 | 7/2015 | Helmlinger |
| 9,242,056 | B2 | 1/2016 | Andersen et al. |
| D757,926 | S | 5/2016 | Van Sickle et al. |
| 9,352,107 | B2 | 5/2016 | Von Hollen et al. |
| 9,427,534 | B2 | 8/2016 | Bruin et al. |
| 9,452,317 | B2 | 9/2016 | Arkush |
| 9,468,729 | B2 | 10/2016 | Sutherland et al. |
| D771,800 | S | 11/2016 | Engelhard et al. |
| 9,555,202 | B2 | 1/2017 | Von Hollen et al. |
| 9,764,104 | B2 | 9/2017 | Gumaste et al. |
| 9,782,551 | B2 | 10/2017 | Morrison et al. |
| 10,016,567 | B2 | 7/2018 | Denyer et al. |
| 10,406,302 | B2 | 9/2019 | Andrade et al. |
| 10,675,422 | B2 | 6/2020 | Morrison et al. |
| 10,814,078 | B2 | 10/2020 | Ciancone et al. |
| 2002/0029779 | A1 | 3/2002 | Schmidt et al. |
| 2002/0090601 | A1 | 7/2002 | Strupat et al. |
| 2003/0075171 | A1 | 4/2003 | Jones et al. |
| 2003/0159694 | A1 | 8/2003 | McNaughton |
| 2004/0007231 | A1 | 1/2004 | Zhou |
| 2005/0087178 | A1 | 4/2005 | Milton |
| 2005/0087189 | A1 | 4/2005 | Crockford et al. |
| 2006/0089545 | A1 | 4/2006 | Ratjen et al. |
| 2007/0017506 | A1 | 1/2007 | Bell et al. |
| 2007/0125372 | A1 | 6/2007 | Chen |
| 2009/0194104 | A1 | 8/2009 | Van Sickle |
| 2009/0314292 | A1 | 12/2009 | Overfield et al. |
| 2010/0191192 | A1 | 7/2010 | Prasad et al. |
| 2010/0192948 | A1 | 8/2010 | Sutherland et al. |
| 2010/0250280 | A1 | 9/2010 | Sutherland |
| 2010/0252036 | A1 | 10/2010 | Sutherland et al. |
| 2010/0324439 | A1 | 12/2010 | Davenport |
| 2011/0180563 | A1 | 7/2011 | Fitchett et al. |
| 2011/0226237 | A1 | 9/2011 | Morrison |
| 2011/0226242 | A1 | 9/2011 | Von Hollen et al. |
| 2012/0012106 | A1 | 1/2012 | Bari |
| 2012/0165693 | A1 | 6/2012 | Williams et al. |
| 2012/0240923 | A1 | 9/2012 | Denyer et al. |
| 2012/0285236 | A1 | 11/2012 | Haartsen et al. |
| 2012/0291779 | A1 | 11/2012 | Haartsen et al. |
| 2012/0312302 | A1 | 12/2012 | Cardelius et al. |
| 2013/0008436 | A1* | 1/2013 | Von Hollen ........ A61M 15/009 128/200.14 |
| 2013/0053719 | A1 | 2/2013 | Wekell |
| 2013/0092158 | A1 | 4/2013 | Levy et al. |
| 2013/0151162 | A1 | 6/2013 | Harris et al. |
| 2013/0186392 | A1 | 7/2013 | Haartsen et al. |
| 2013/0186393 | A1* | 7/2013 | Von Hollen ........ A61M 16/208 128/200.23 |
| 2014/0000598 | A1 | 1/2014 | Sutherland et al. |
| 2014/0000599 | A1 | 1/2014 | Dyche et al. |
| 2014/0106324 | A1 | 4/2014 | Adams et al. |
| 2014/0182584 | A1 | 7/2014 | Sutherland et al. |
| 2014/0257126 | A1 | 9/2014 | Vink et al. |
| 2014/0311492 | A1 | 10/2014 | Stuebiger et al. |

(56) References Cited

U.S. PATENT DOCUMENTS

| | | | |
|---|---|---|---|
| 2014/0318534 A1 | 10/2014 | Engelbreth | |
| 2014/0352690 A1 | 12/2014 | Kolb et al. | |
| 2015/0011906 A1 | 1/2015 | Wallach | |
| 2015/0059739 A1 | 3/2015 | Aslam | |
| 2015/0061867 A1 | 3/2015 | Engelhard et al. | |
| 2015/0099994 A1 | 4/2015 | Spencer et al. | |
| 2015/0100276 A1 | 4/2015 | Huang et al. | |
| 2015/0100335 A1 | 4/2015 | Engelhard et al. | |
| 2015/0112707 A1 | 4/2015 | Manice et al. | |
| 2015/0122261 A1 | 5/2015 | Pettit | |
| 2015/0164373 A1 | 6/2015 | Davis et al. | |
| 2015/0174348 A1 | 6/2015 | Tunnell et al. | |
| 2015/0174349 A1 | 6/2015 | Tunnell et al. | |
| 2015/0235548 A1 | 8/2015 | Engelhard et al. | |
| 2015/0273165 A1 | 10/2015 | Hadash | |
| 2015/0283337 A1 | 10/2015 | Adams et al. | |
| 2015/0352281 A1 | 10/2015 | Pfrang | |
| 2015/0320958 A1 | 11/2015 | Metysek et al. | |
| 2016/0045681 A1 | 2/2016 | Cheatham, III et al. | |
| 2016/0045682 A1 | 2/2016 | Boyden et al. | |
| 2016/0045683 A1 | 2/2016 | Cheatham, III et al. | |
| 2016/0045685 A1 | 2/2016 | Hyde et al. | |
| 2016/0051776 A1 | 2/2016 | Von Hollen | |
| 2016/0058960 A1 | 3/2016 | Papania et al. | |
| 2016/0082208 A1 | 3/2016 | Ballam et al. | |
| 2016/0106375 A1 | 4/2016 | Leydon | |
| 2016/0106935 A1 | 4/2016 | Sezan et al. | |
| 2016/0129182 A1 | 5/2016 | Schuster et al. | |
| 2016/0129206 A1 | 5/2016 | Engelbreth | |
| 2016/0136366 A1 | 5/2016 | Bennett | |
| 2016/0136367 A1 | 5/2016 | Varney | |
| 2016/0144141 A1 | 5/2016 | Biwas et al. | |
| 2016/0144142 A1 | 5/2016 | Baker et al. | |
| 2016/0166766 A1 | 6/2016 | Schuster et al. | |
| 2016/0184535 A1 | 6/2016 | Edwards et al. | |
| 2016/0193436 A1 | 7/2016 | Khasawneh | |
| 2016/0213868 A1 | 7/2016 | Khasawneh et al. | |
| 2016/0256639 A1 | 9/2016 | Van Sickle et al. | |
| 2016/0287139 A1 | 10/2016 | Luttrell | |
| 2016/0314256 A1 | 10/2016 | Su et al. | |
| 2016/0325058 A1 | 11/2016 | Samson et al. | |
| 2016/0331917 A1 | 11/2016 | Bennett et al. | |
| 2016/0339187 A1 | 11/2016 | Smaldone | |
| 2016/0339190 A1 | 11/2016 | Morrison et al. | |
| 2016/0354562 A1 | 12/2016 | Morrison | |
| 2017/0020776 A1 | 1/2017 | Khasawneh et al. | |
| 2017/0127945 A1 | 5/2017 | Reed | |
| 2017/0173282 A1 | 6/2017 | O'Sullivan et al. | |
| 2017/0296772 A1 | 10/2017 | Costella et al. | |
| 2017/0333645 A1* | 11/2017 | Alizoti | A61M 15/002 |
| 2017/0333661 A1 | 11/2017 | Bennett et al. | |
| 2018/0008790 A1 | 1/2018 | Costella et al. | |
| 2018/0264207 A1* | 9/2018 | Von Hollen | A61M 16/20 |
| 2019/0160237 A1 | 5/2019 | O'Callaghan et al. | |
| 2019/0366019 A1 | 12/2019 | Meyer et al. | |
| 2020/0001026 A1 | 1/2020 | Starr et al. | |
| 2020/0345588 A1 | 11/2020 | Merrell et al. | |

FOREIGN PATENT DOCUMENTS

| | | |
|---|---|---|
| DE | 102010024912 B4 | 2/2013 |
| EP | 0387222 B1 | 7/1993 |
| EP | 0824023 A1 | 2/1998 |
| EP | 0617628 B1 | 5/1998 |
| EP | 1338296 A1 | 8/2003 |
| EP | 1330283 B1 | 9/2006 |
| EP | 1993642 B1 | 1/2012 |
| EP | 1670533 B1 | 7/2012 |
| EP | 2300083 B1 | 5/2013 |
| EP | 2609954 A2 | 7/2013 |
| EP | 2376156 B1 | 1/2014 |
| EP | 2859906 A1 | 4/2015 |
| EP | 2563436 B1 | 10/2015 |
| EP | 2512566 B1 | 5/2016 |
| EP | 1613214 B1 | 10/2016 |
| EP | 3053620 A3 | 10/2016 |
| EP | 3097937 A1 | 11/2016 |
| GB | 2262452 A | 6/1993 |
| GB | 2263068 A | 7/1993 |
| GB | 2406283 A | 3/2005 |
| GB | 2479953 A | 2/2011 |
| GB | 2490770 A | 11/2012 |
| GB | 2512047 A | 9/2014 |
| GB | 2479953 B | 4/2015 |
| WO | WO9010470 A1 | 9/1990 |
| WO | WO9207599 A1 | 5/1992 |
| WO | WO 92/17231 A1 | 10/1992 |
| WO | WO9312823 A2 | 7/1993 |
| WO | WO9507723 A1 | 3/1995 |
| WO | WO9522365 A1 | 8/1995 |
| WO | WO 1996/037249 A1 | 11/1996 |
| WO | WO9729799 A2 | 8/1997 |
| WO | WO9911310 A1 | 3/1999 |
| WO | WO0205879 A1 | 1/2002 |
| WO | WO0209574 A2 | 2/2002 |
| WO | WO02058771 A1 | 8/2002 |
| WO | WO03020349 A2 | 3/2003 |
| WO | WO03063937 A1 | 8/2003 |
| WO | WO03092576 A2 | 11/2003 |
| WO | WO03107523 A1 | 12/2003 |
| WO | WO2005042076 A1 | 5/2005 |
| WO | WO2005074455 A2 | 8/2005 |
| WO | WO2006123956 A1 | 11/2006 |
| WO | WO2007101438 A1 | 9/2007 |
| WO | WO2008112353 A2 | 9/2008 |
| WO | WO2009022139 A1 | 2/2009 |
| WO | WO2010023591 A2 | 3/2010 |
| WO | WO2010023591 A3 | 3/2010 |
| WO | WO2010110682 A1 | 9/2010 |
| WO | WO2010114392 A1 | 10/2010 |
| WO | WO2011003017 A1 | 1/2011 |
| WO | WO2011073806 A1 | 6/2011 |
| WO | WO2011083377 A1 | 7/2011 |
| WO | WO2011089486 A1 | 7/2011 |
| WO | WO2011089489 A1 | 7/2011 |
| WO | WO2011089490 A1 | 7/2011 |
| WO | WO2011130183 A2 | 10/2011 |
| WO | WO2011130583 A2 | 10/2011 |
| WO | WO2011135353 A1 | 11/2011 |
| WO | WO2012038861 A1 | 3/2012 |
| WO | WO2012064540 A2 | 5/2012 |
| WO | WO2012173992 A1 | 12/2012 |
| WO | WO2013028705 A2 | 2/2013 |
| WO | WO2013042002 A1 | 3/2013 |
| WO | WO2013043063 A1 | 3/2013 |
| WO | WO2013061240 A1 | 5/2013 |
| WO | WO2013061248 A1 | 5/2013 |
| WO | WO2013098334 A1 | 7/2013 |
| WO | WO2013124624 A1 | 8/2013 |
| WO | WO2014004437 A1 | 1/2014 |
| WO | WO2014033229 A1 | 3/2014 |
| WO | WO2014147550 A1 | 9/2014 |
| WO | WO2014202923 A1 | 12/2014 |
| WO | WO2014204511 A2 | 12/2014 |
| WO | WO2015002652 A1 | 1/2015 |
| WO | WO2015004554 A1 | 1/2015 |
| WO | WO2015004559 A2 | 1/2015 |
| WO | WO2015006701 A2 | 1/2015 |
| WO | WO2015008013 A1 | 1/2015 |
| WO | WO2015022595 A1 | 2/2015 |
| WO | WO2015030610 A2 | 3/2015 |
| WO | WO2015030610 A3 | 3/2015 |
| WO | WO2015031472 A1 | 3/2015 |
| WO | WO2015036723 A1 | 3/2015 |
| WO | WO2015052519 A1 | 4/2015 |
| WO | WO2015104522 A1 | 7/2015 |
| WO | WO2015109259 A1 | 7/2015 |
| WO | WO2015114285 A1 | 8/2015 |
| WO | WO2015128173 A1 | 9/2015 |
| WO | WO2015133909 A1 | 9/2015 |
| WO | WO2015138454 A1 | 9/2015 |
| WO | WO2015144442 A1 | 10/2015 |
| WO | WO2015150029 A1 | 10/2015 |
| WO | WO2015154864 A2 | 10/2015 |

(56) References Cited

FOREIGN PATENT DOCUMENTS

| WO | WO2015154865 A2 | 10/2015 |
|---|---|---|
| WO | WO2015174856 A1 | 11/2015 |
| WO | WO2015178907 A1 | 11/2015 |
| WO | WO2016025553 A1 | 2/2016 |
| WO | WO2016030521 A1 | 3/2016 |
| WO | WO2016033419 A1 | 3/2016 |
| WO | WO2016033421 A1 | 3/2016 |
| WO | WO2016043601 A1 | 3/2016 |
| WO | WO2016048435 A1 | 3/2016 |
| WO | WO2016049066 A1 | 3/2016 |
| WO | WO2016060863 A3 | 4/2016 |
| WO | WO 2016/079461 A1 | 5/2016 |
| WO | WO2016075525 A1 | 5/2016 |
| WO | WO2016081294 A1 | 5/2016 |
| WO | WO2016085988 A2 | 6/2016 |
| WO | WO2016090260 A1 | 6/2016 |
| WO | WO 2016/110804 A1 | 7/2016 |
| WO | WO2016111633 A1 | 7/2016 |
| WO | WO2016116591 A1 | 7/2016 |
| WO | WO2016162699 A1 | 10/2016 |
| WO | WO2016165029 A1 | 10/2016 |
| WO | WO2016181048 A1 | 11/2016 |
| WO | WO 2017/071879 A1 | 5/2017 |
| WO | WO 2017/163211 A1 | 9/2017 |
| WO | WO 2017/178776 A1 | 10/2017 |
| WO | WO 2017/187116 A1 | 11/2017 |
| WO | WO 2017/194906 A1 | 11/2017 |
| WO | WO 2017/199215 A1 | 11/2017 |
| WO | WO 2021/255202 A1 | 12/2021 |

OTHER PUBLICATIONS

International Search Report in International Application No. PCT/IB2017/052968 dated Sep. 5, 2017, 7 pages.
International Search Report and Written Opinion in International Application No. PCT/IB2019/054580 dated Nov. 5, 2019, 9 pages.
International Search Report and Written Opinion in International Application No. PCT/IB2017/055603 dated Jan. 5, 2018, 10 pgs.
Cipla, "Revolizer Inhaler for Asthma Treatment", https://www.youtube.com/watch?v=2xrl14KQITw, YouTube, Sep. 14, 2010.
European Search Report for Application No. 19814765.4 dated Feb. 3, 2022 (9 pages).

* cited by examiner

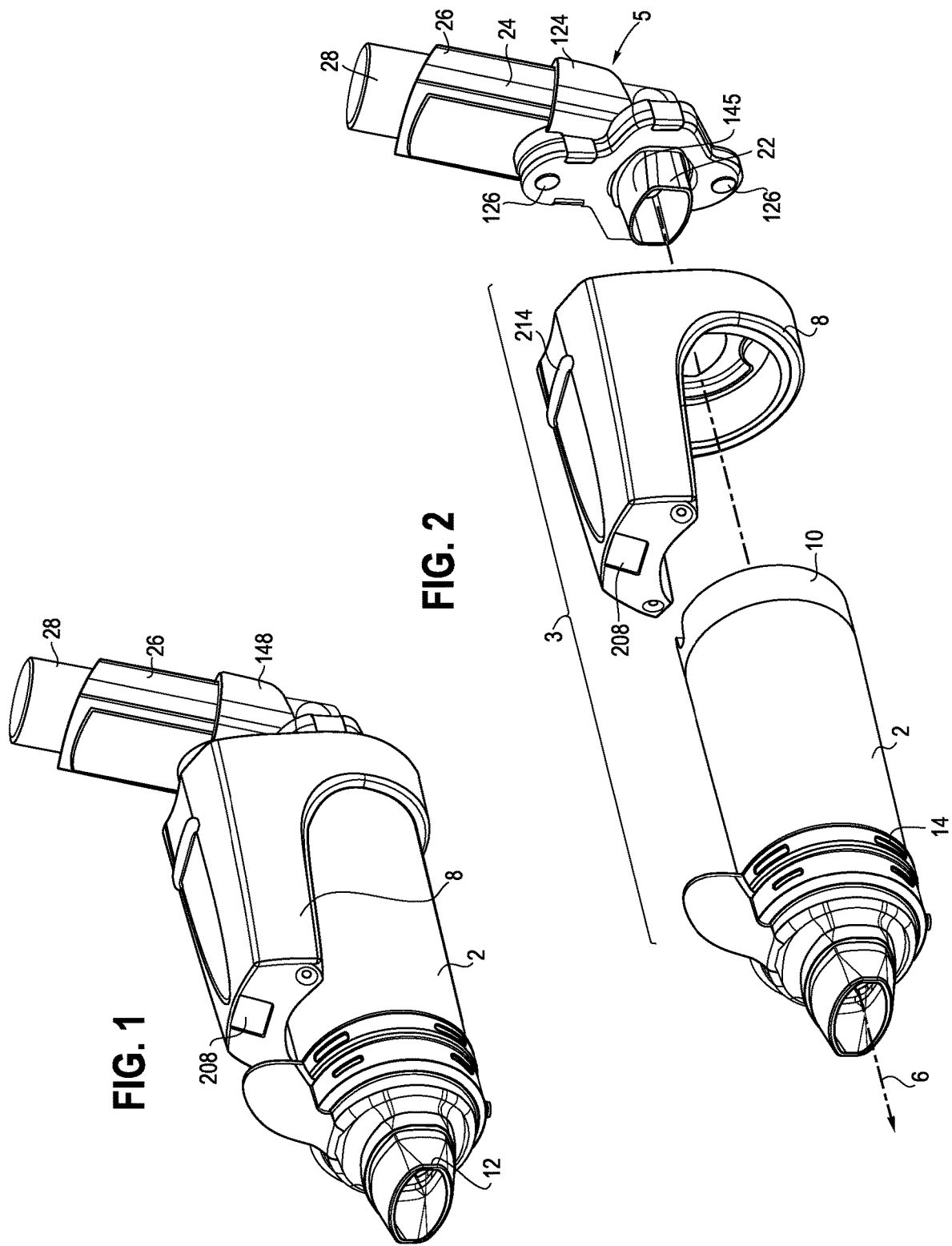

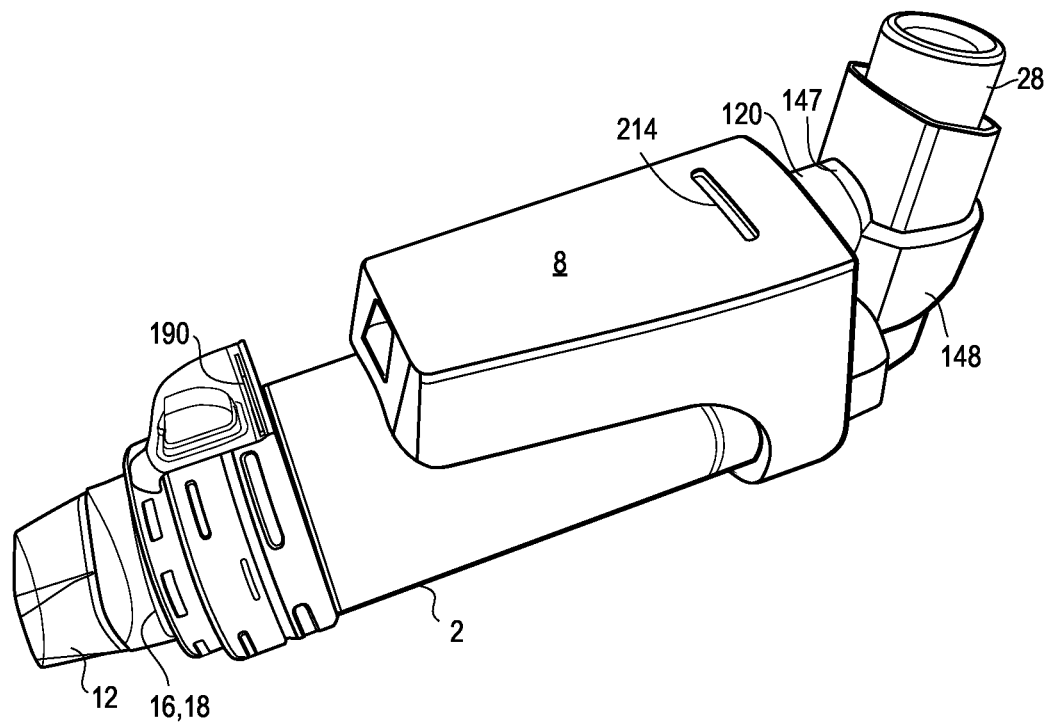
FIG. 3A
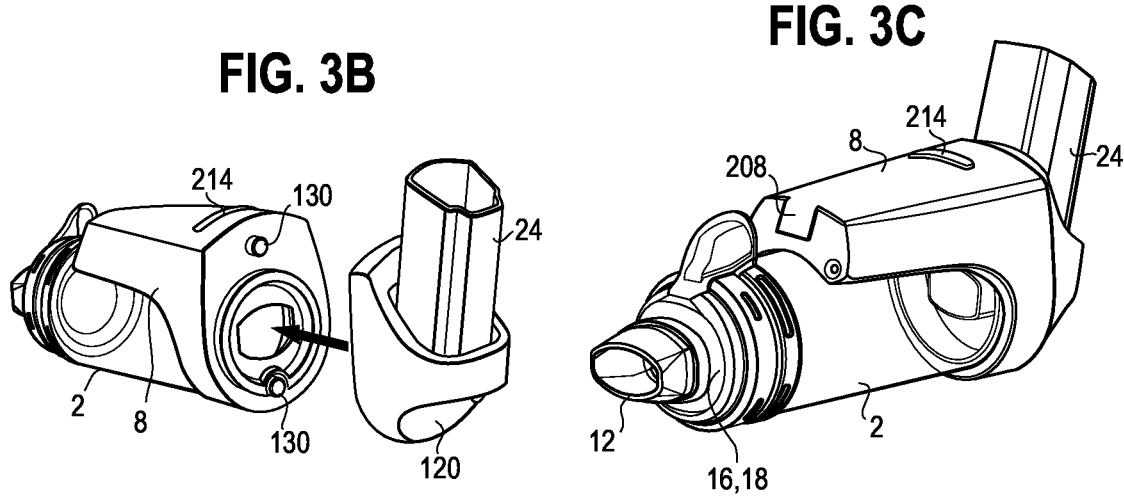
FIG. 3B
FIG. 3C

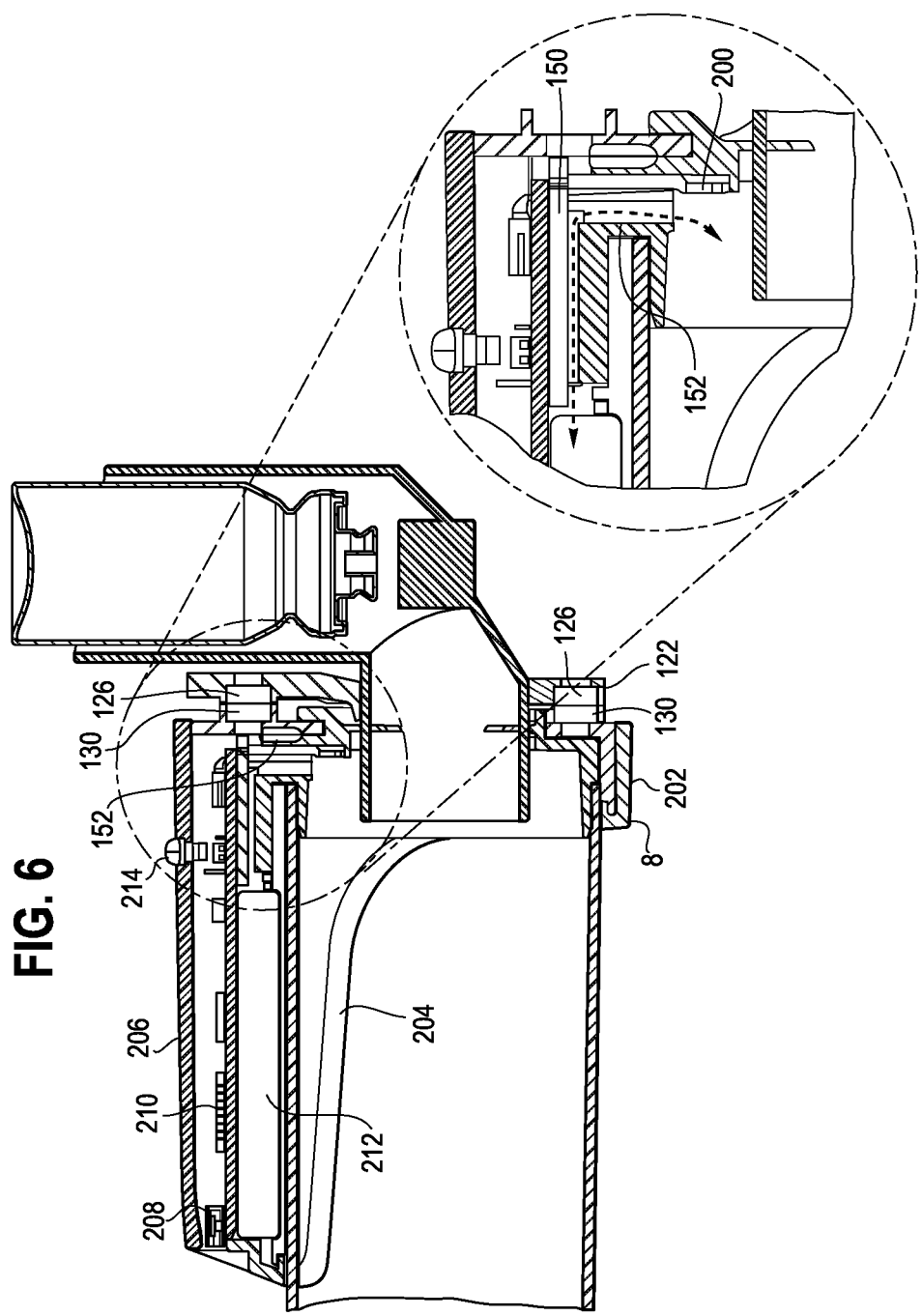

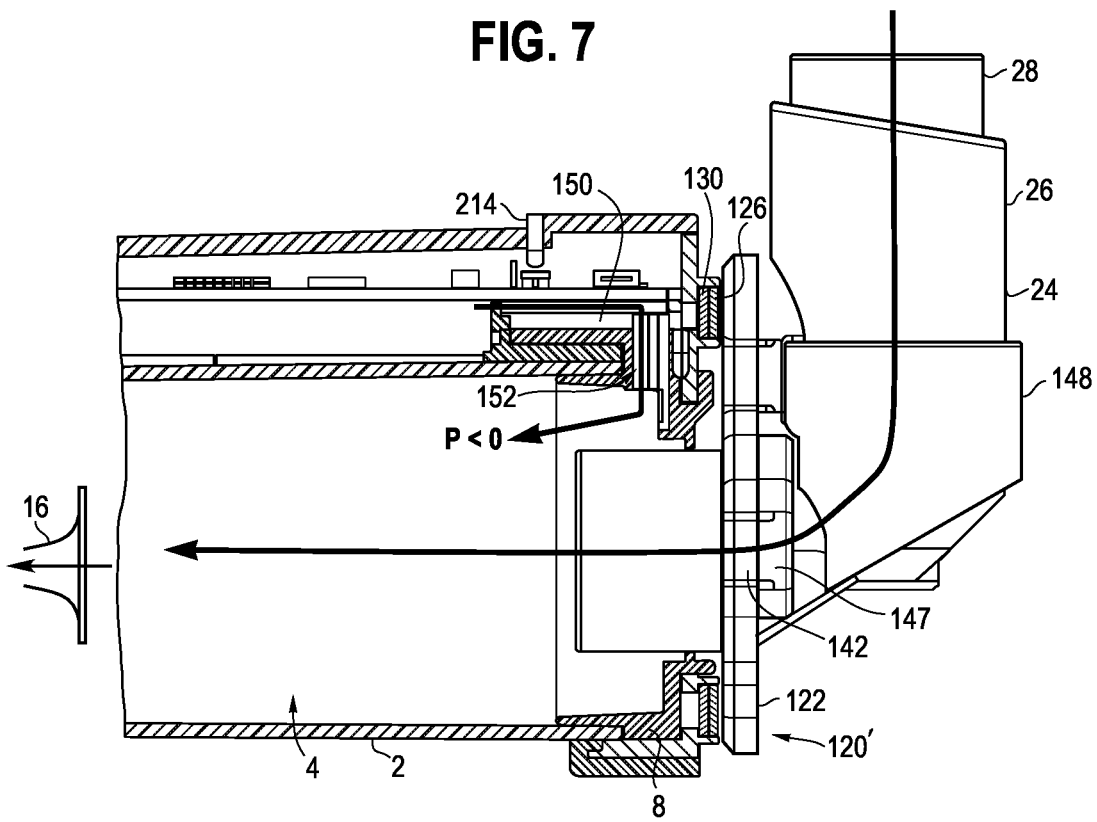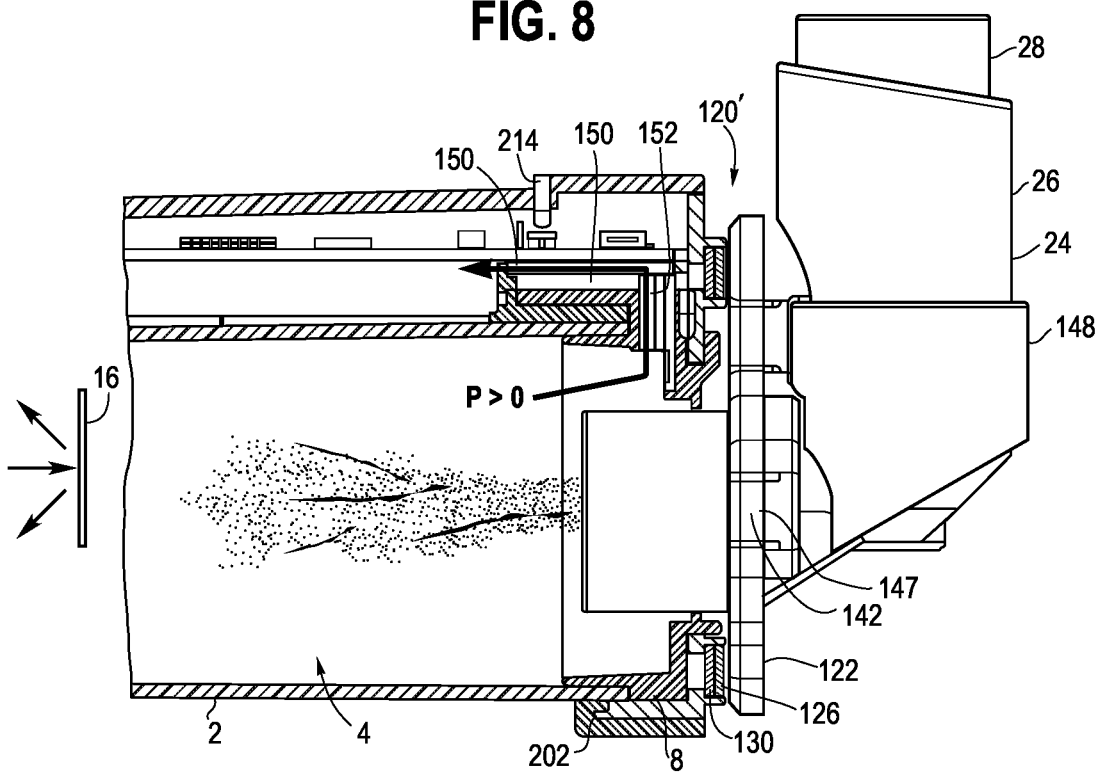

SMART VALVED HOLDING CHAMBER

BACKGROUND

This application is a continuation of U.S. application Ser. No. 16/429,674, filed Jun. 3, 2019 and entitled "Smart Valved Holding Chamber," which application claims the benefit of U.S. Provisional Application No. 62/680,232, filed Jun. 4, 2018, the entire disclosures of which hereby incorporated herein by reference.

FIELD OF THE INVENTION

This application is directed to devices and systems for use in the field of pulmonary aerosol drug delivery via a metered dose inhaler (MDI) and valved holding chamber (VHC), and in particular devices and systems for improving patient adherence to their medication regimen and providing feedback to the user, prescriber or payer regarding proper inhalation technique and end of treatment.

VHC and MDI systems are typically used to treat such conditions as asthma, COPD and cystic fibrosis. Patients being treated for such conditions may exhibit poor adherence to medication or therapy regimes, practice improper device technique and/or fail to receive feedback about dose assurance. These types of problems may create additional cost burdens for the healthcare system with less than optimal patient outcomes.

Medication compliance is often difficult to monitor, although this information is invaluable to healthcare and insurance providers. Currently, there is no way to actively monitor a patient's use of a VHC, and despite the recent advent of smart inhalers, most MDI's are not able to monitor and communicate medication use on their own. Therefore, the need exists for a VHC that is capable of monitoring medication usage, as well as providing feedback to the user and healthcare and insurance providers.

While in some applications, each inhaler is outfitted with a smart device, such systems are costly.

BRIEF SUMMARY

Upon insertion of an MDI into a VHC, the system identifies the MDI being inserted in the VHC. Once the MDI is actuated, the system detects and records the actuation. This information is used to provide coordination feedback following the current treatment and/or at the beginning of subsequent treatments. The system also may detect when the device is not operating optimally, for example when the inhalation/exhalation valve is not properly functioning, for example if the valve is torn, dislodged, stuck open or otherwise disabled.

Over time, the system may also provide feedback to the user or caregiver about when the device should be cleaned or replaced, for example due to build-up of residue on the inside of the holding chamber. The system may also provide feedback regarding adherence to inhalation technique, for example analyzing the user's inhalation characteristics, which may include the length of inhalation and the number of breathes taken for each inhaler actuation.

The various systems and devices improve patient adherence, improve device technique and provide dose assurance. These aspect, in turn, help reduce costs for healthcare systems and providers (payers) by ensuring proper adherence. In addition, healthcare providers (prescribers), having reliable information about adherence and usage, may then rely on the patient specific data to make informed decisions about treatment protocol and changes. The patients, in turn, receive maximum benefit from the treatment, while also reducing out of pocket costs.

In one aspect, a medication delivery system including a holding chamber having an input and an output end, a backpiece coupled to the input end of the holding chamber and having an electrical circuit and an opening. An MDI incudes an insert portion moveable between an engaged position wherein the insert portion is received in the opening and a disengaged position wherein the insert portion is removed from the opening, and at least one contact that completes the electrical circuit when the insert portion is in the engaged position.

In another aspect, one embodiment of an identification accessory for coupling an MDI to a holding chamber includes a faceplate having an opening shaped to receive an insert portion of the MDI and an adapter releasably coupled to the faceplate, the adapter comprising a retention member shaped to engage the MDI.

In another aspect, a method of assembling a medication delivery system includes coupling a backpiece to an input end of a holding chamber, wherein the backpiece includes an electrical circuit and defines an opening to an interior of the holding chamber, inserting an insert portion of an MDI through the opening of the backpiece, and completing the electrical circuit with at least one contact disposed on the MDI.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

The Figures show different embodiments of medication delivery systems, block/flow diagrams and methods for use and assembly thereof.

FIG. 1 is a perspective view of one embodiment of a smart VHC with an MDI applied coupled thereto.

FIG. 2 is an exploded view of the embodiment of the smart VHC and MDI shown in FIG. 1.

FIGS. 3A and B are top and front perspective views of one embodiment of a smart VHC respectively.

FIG. 3C is a rear exploded view of one embodiment of a smart VHC.

FIG. 6 is a cross-sectional view of a smart VHC adapter fitted on a holding chamber.

FIG. 7 is a partial cross-sectional view of a smart VHC during inspiration.

FIG. 8 is a partial cross-sectional view of a smart VHC during inhaler actuation.

DETAILED DESCRIPTION OF THE DRAWINGS AND THE PRESENTLY PREFERRED EMBODIMENTS

Figure 4A:
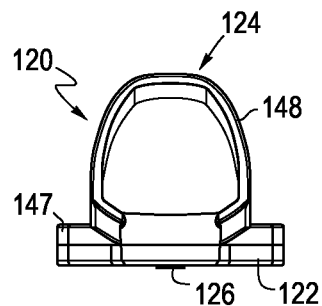
FIGS. 4A and B are top views of different embodiments of a MDI adapter for use with the smart VHC.
Figure 4B:
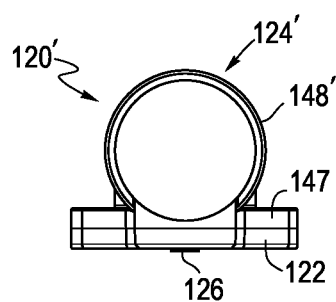
FIGS. 4C-E are perspective, front and side views of one embodiment of the MDI adapter shown in FIG. 4A.
FIG. 4F is a cross-sectional view of the MDI adapter taken along line 4F in FIG. 4D.
Figure 4C:
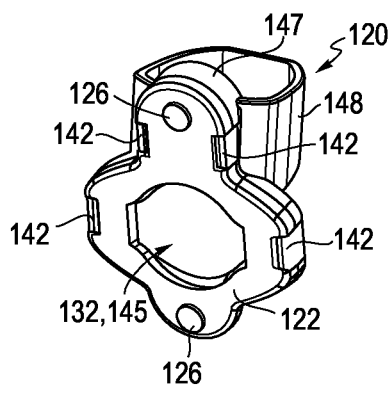
Figure 4D:
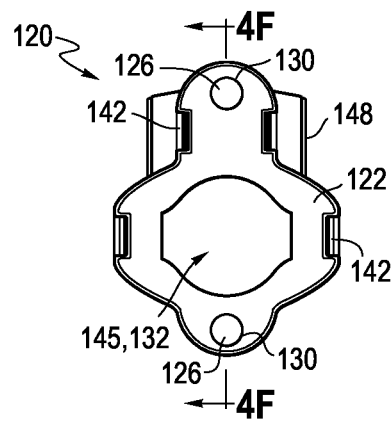
Figure 4E:
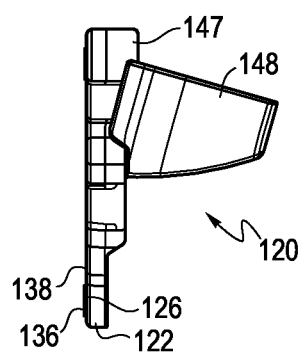
Figure 4F:
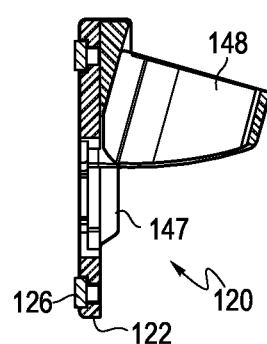
Figure 5:
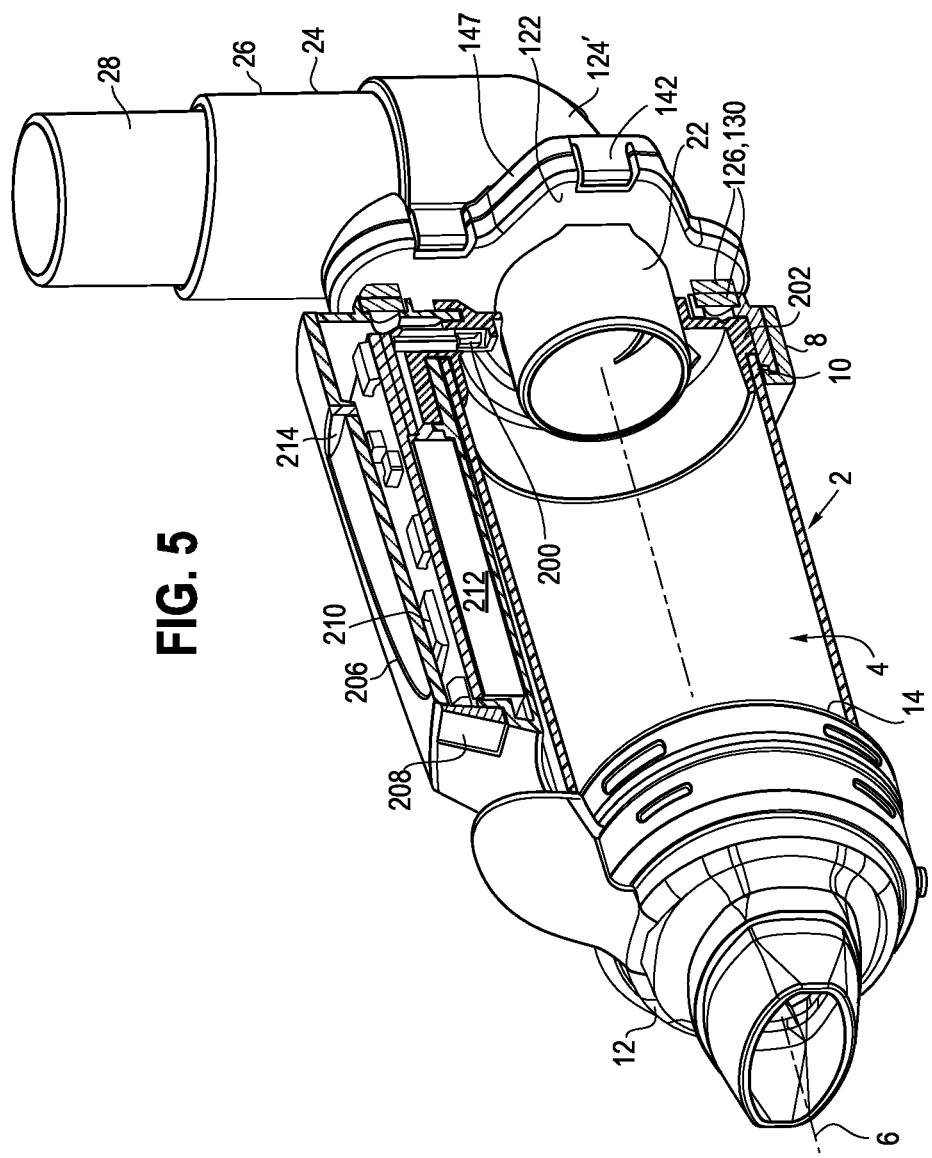
FIG. 5 is a partial cut-away perspective view of the smart VHC shown in FIG. 1.

It should be understood that the term "plurality," as used herein, means two or more. The term "coupled" means connected to or engaged with whether directly or indirectly, for example with an intervening member, and does not require the engagement to be fixed or permanent, although it may be fixed or permanent (or integral), and includes both mechanical and electrical connection. The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first component may be the same as a second component, with each simply being applicable to separate but identical components.

In a traditional patient/prescriber/payer model, the patient is prescribed a therapy and purchases the medications and/or therapy device. If the purchase is covered by a payer, there typically is no feedback to the payer that the therapy is being performed correctly and as prescribed, aside from future requests for additional therapies. The patient typically is trained on the use of the medical device by a prescriber and then asked to use the device in their daily life. At some point, the patient may follow up with the prescriber because of a condition change, a prescription refill, or perhaps at a set frequency. At such a time, the prescriber may evaluate the effectiveness of the treatment and decide to modify or continue therapy. If the prescriber decides to modify the therapy, then a new prescription is given and the cycle repeated. Some of the technical challenges faced in improving adherence to treatment regimens, that in turn may lead to improved cost tracking and diagnosis, include challenges in the ability to effectively monitor the functions of different therapeutic devices and the usage of the device, how to then provide an effective real-time feedback to a user and/or a prescriber, and how to make real-time changes to the performance of the device and/or behavior/technique of the user in certain instances.

Referring to FIGS. 1-3, various smart devices, and feedback associated therewith, may be introduced to improve the effectiveness of the therapy. In addition, the prescriber is provided patient-specific data to make informed decisions about treatment, including the modification thereof, and the payer is provided with an assurance that the patient has adhered to the treatment regimen before covering the costs of another prescription. Various aspects of a smart VHC, communication and computer system and other components of the assembly thereof, are disclosed in US 2017/0333645 A1, entitled "Smart Valved Holding Chamber" and assigned to Trudell Medical International, with the entire disclosure thereof being hereby incorporated herein by reference.

Referring to FIGS. 3A-C, 5, 6, 15 and 18, one exemplary embodiment of a smart VHC includes a chamber housing 2 having a wall defining an interior space 4 extending along a longitudinal axis/inhalation flow path 6, a back piece 8 coupled to an input end 10 of the chamber housing and a mouthpiece and/or valve assembly 12 coupled to an output end 14 of the chamber housing. The mouthpiece assembly may be releasably and removably coupled to the chamber housing, for example with tabs received in grooves. The mouthpiece is configured with an inhalation valve 16 and/or an exhalation valve 18, which provides an exhalation flow path 13. The inhalation and exhalation valves may alternatively be disposed on other components of the VHC. In various embodiments, a valve is configured as part of an annular donut valve, having an inner periphery that defines the inhalation valve 16 and an outer periphery defining an exhalation valve 18. In other embodiments, the inhalation valve is configured as a duckbill valve, which may also have an outer annular flange defining the exhalation valve. In other embodiments, the inhalation and exhalation valves may not be integral, but rather are separately formed and disposed within the VHC. The backpiece 8 is configured with an opening 20, which is shaped to receive a mouthpiece portion 22 of a MDI actuation boot 24. The boot further includes a chimney portion 26 defining a cavity shaped to receive a medicament container 28. The boot further includes a support block defining a well shaped to receive a valve stem of the MDI. The well communicates with an orifice, which releases aerosolized medication into the interior space of the chamber housing. Various embodiments of the VHC and MDI, including the mouthpiece assembly, chamber housing and backpiece, are disclosed for example and without limitation in U.S. Pat. Nos. 6,557,549, 7,201, 165, 7,360,537 and 8,550,067, all assigned to Trudell Medical International, the Assignee of the present application, with the entire disclosures of the noted patents being hereby incorporated herein by reference.

Communication and Data Processing

In seeking to satisfy these propositions, the device, such as a VHC associated with an MDI, may be configured to perform one or more of the following: (1) correctly identify the MDI being used with the VHC, (2) correctly identify when the MDI has been actuated, (3) monitor and provide feedback to the user regarding proper technique and (4) provide patient specific data to the prescriber and/or provider. Referring to FIGS. 19 and 22-24, one aspect of the embodiments relates to the handling of data. Data logged by the VHC and/or MDI may be transferred to an external device, such as a smartphone, tablet, personal computer, etc. If such an external device is unavailable, the data may be stored internally in the VHC and/or MDI in a data storage module or other memory and transferred upon the next syncing between the VHC/MDI and external device. Software may accompany the VHC/MDI to implement the data transfer and analysis.

In order to provide faster and more accurate processing of the data, for example from one or more various sensors, generated within the smart VHC and/or MDI, data may be wirelessly communicated to a smart phone, local computing device and/or remote computing device to interpret and act on the raw sensor data.

In one implementation, the smart VHC and/or MDI includes circuitry for transmitting raw sensor data in real-time to a local device, such as a smart phone. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the smart VHC.

In addition to simply presenting data, statistics or instructions on a display of the smart phone or other local computer in proximity of the smart VHC and/or MDI, proactive operations relating to the smart VHC and/or MDI may be actively managed and controlled. For example, if the smart phone or other local computer in proximity to the smart VHC and/or MDI determines that the sensor data indicates the end of treatment has been reached, or that further treatment is needed, the smart phone or other local computing device may communicate such information directly to the patient. Other variations are also contemplated, for example where a remote server in communication with the smart phone, or in direct communication with the smart VHC and/or MDI via a communication network, can supply the information and instructions to the patient/user.

In yet other implementations, real-time data gathered in the smart VHC and/or MDI and relayed via to the smart phone to the remote server may trigger the remote server to track down and notify a physician or supervising caregiver regarding a problem with the particular treatment session or a pattern that has developed over time based on past treatment sessions for the particular user. Based on data from the one or more sensors in the smart VHC and/or MDI, the remote server may generate alerts to send via text, email or other electronic communication medium to the user, the user's physician or other caregiver.

Figure 22:
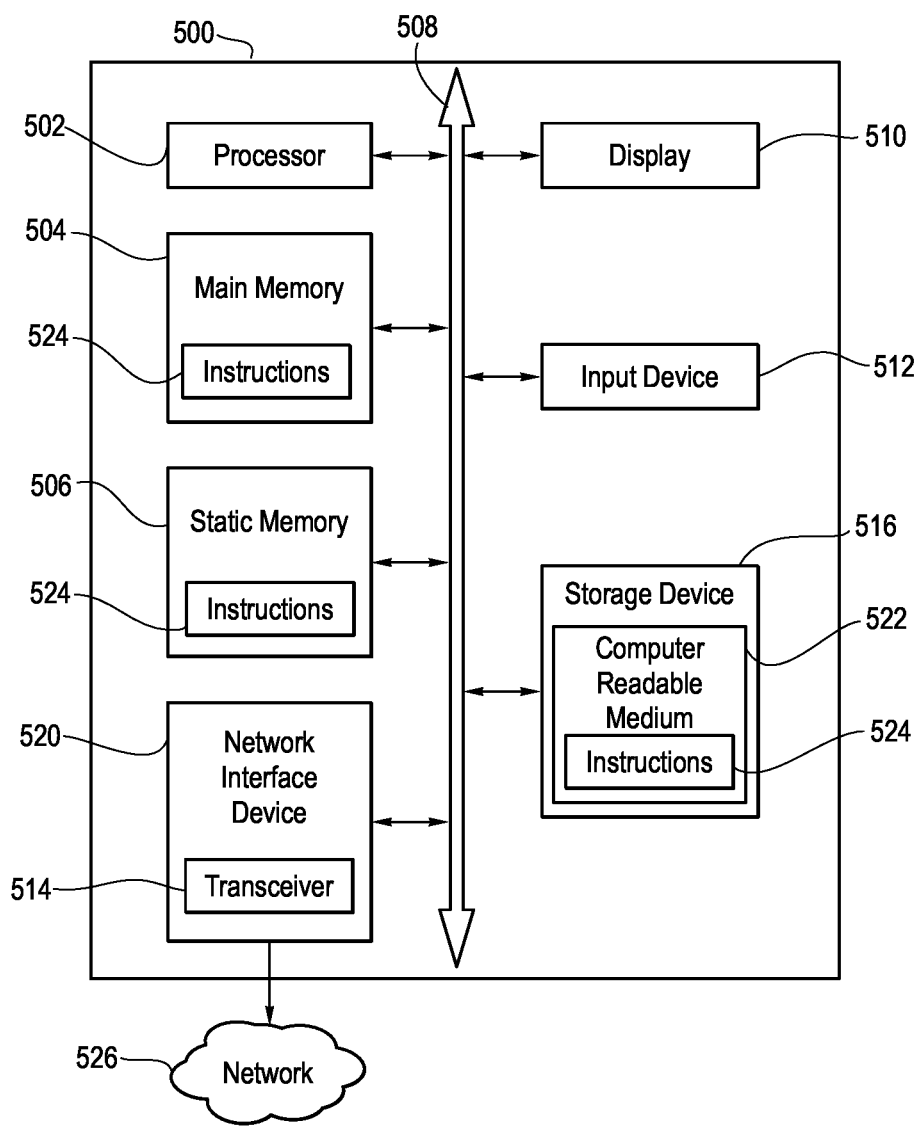
FIG. 22 is a schematic illustrating the computer structure.
Figure 23:
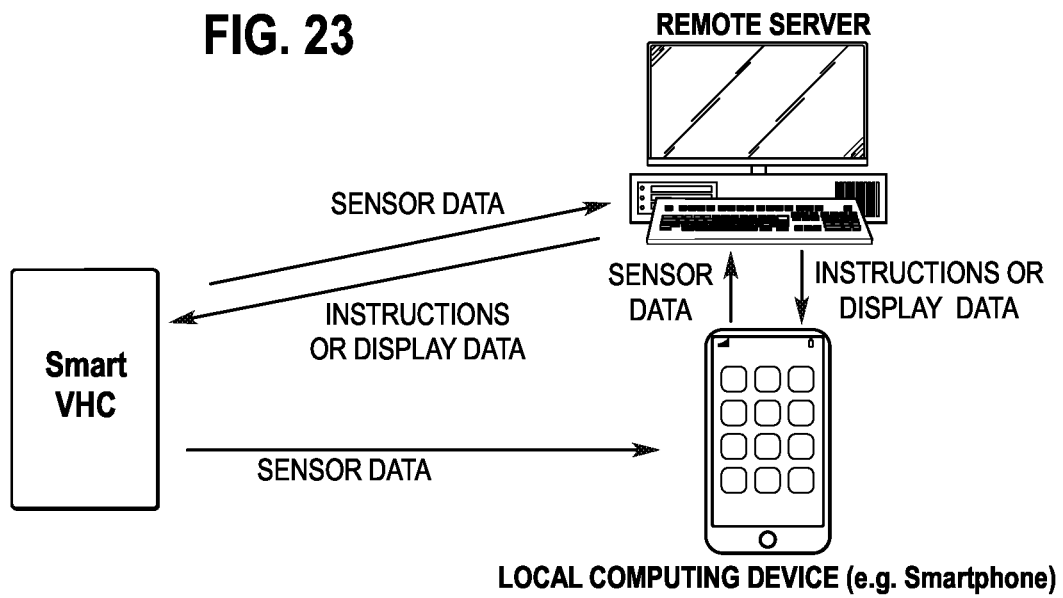
FIG. 23 is a schematic illustration of a communication system.
Figure 24:
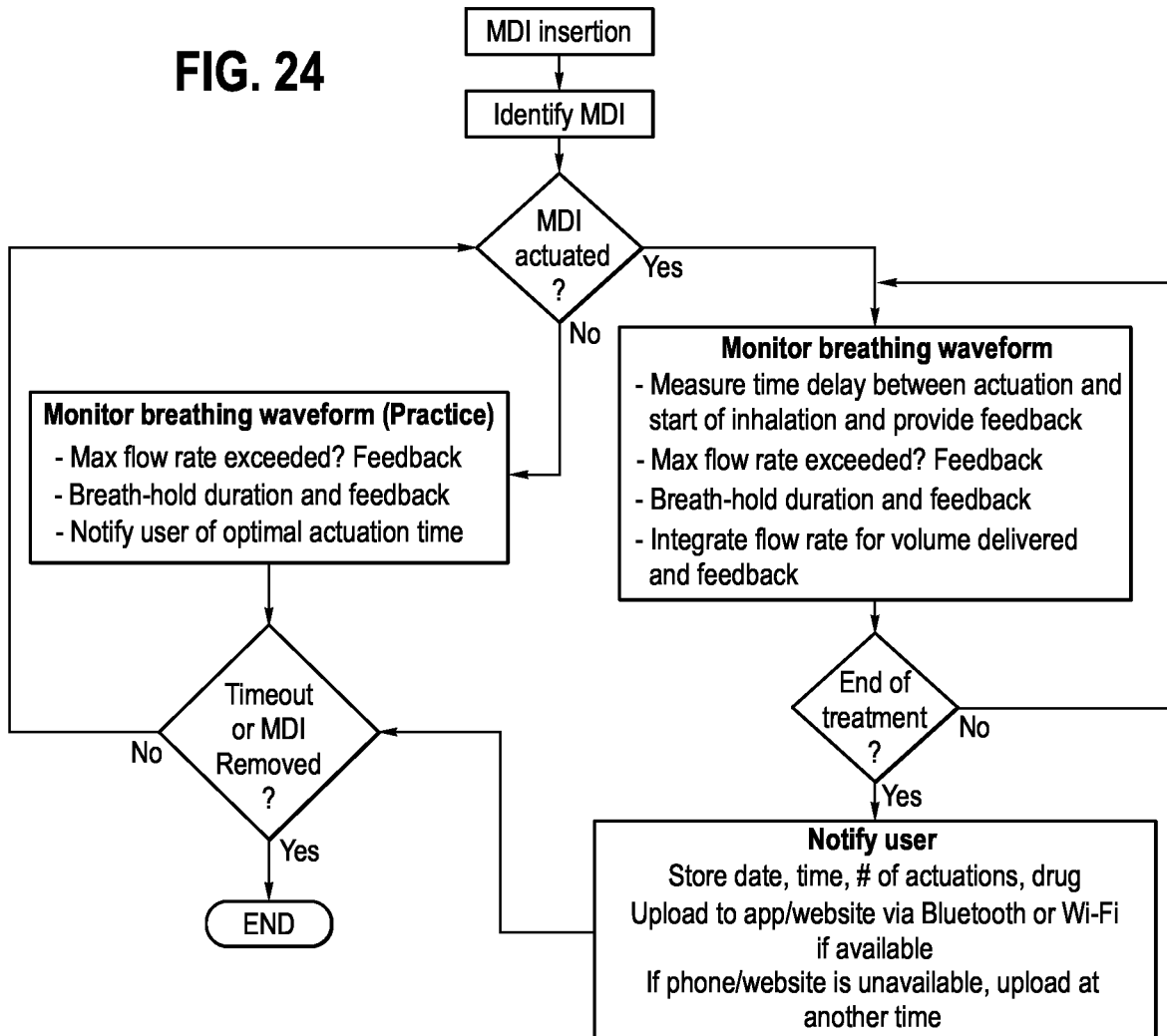
FIG. 24 is a flow chart showing usage protocol of a smart VHC and MDI.

The electronic circuitry in the smart VHC and/or MDI, the local computing device and/or the remote server discussed above, may include some or all of the capabilities of a computer 500 in communication with a network 526 and/or directly with other computers. As illustrated in FIGS. 22-24, the computer 500 may include a processor 502, a storage device 516, a display or other output device 510, an input device 512, and a network interface device 520, all connected via a bus 508. A battery 503 is coupled to and powers the computer. The computer may communicate with the network. The processor 502 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor 502 executes instructions and includes that portion of the computer 500 that controls the operation of the entire computer. Although not depicted in FIGS. 22 and 23, the processor 502 typically includes a control unit that organizes data and program storage in memory and transfers data and other information between the various parts of the computer 500. The processor 502 receives input data from the input device 512 and the network 526 reads and stores instructions (for example processor executable code) 524 and data in the main memory 504, such as random access memory (RAM), static memory 506, such as read only memory (ROM), and the storage device 516. The processor 502 may present data to a user via the output device 510.

Although the computer 500 is shown to contain only a single processor 502 and a single bus 508, the disclosed embodiment applies equally to computers that may have multiple processors and to computers that may have multiple busses with some or all performing different functions in different ways.

The storage device 516 represents one or more mechanisms for storing data. For example, the storage device 516 may include a computer readable medium 522 such as read-only memory (ROM), RAM, non-volatile storage media, optical storage media, flash memory devices, and/or other machine-readable media. In other embodiments, any appropriate type of storage device may be used. Although only one storage device 516 is shown, multiple storage devices and multiple types of storage devices may be present. Further, although the computer 500 is drawn to contain the storage device 516, it may be distributed across other computers, for example on a server.

The storage device 516 may include a controller (not shown) and a computer readable medium 522 having instructions 524 capable of being executed on the processor 502 to carry out the functions described above with reference to processing sensor data, displaying the sensor data or instructions based on the sensor data, controlling aspects of the smart VHC and/or MDI to alter its operation, or contacting third parties or other remotely located resources to provide update information to, or retrieve data from those remotely located resources. In another embodiment, some or all of the functions are carried out via hardware in lieu of a processor-based system. In one embodiment, the controller is a web browser, but in other embodiments the controller may be a database system, a file system, an electronic mail system, a media manager, an image manager, or may include any other functions capable of accessing data items. The storage device 516 may also contain additional software and data (not shown), which is not necessary to understand the invention.

The output device 510 is that part of the computer 500 that displays output to the user. The output device 510 may be a liquid crystal display (LCD) well-known in the art of computer hardware. In other embodiments, the output device 510 may be replaced with a gas or plasma-based flat-panel display or a traditional cathode-ray tube (CRT) display. In still other embodiments, any appropriate display device may be used. Although only one output device 510 is shown, in other embodiments any number of output devices of different types, or of the same type, may be present. In an embodiment, the output device 510 displays a user interface. The input device 512 may be a keyboard, mouse or other pointing device, trackball, touchpad, touch screen, keypad, microphone, voice recognition device, or any other appropriate mechanism for the user to input data to the computer 500 and manipulate the user interface previously discussed. Although only one input device 512 is shown, in another embodiment any number and type of input devices may be present.

The network interface device 520 provides connectivity from the computer 500 to the network 526 through any suitable communications protocol. The network interface device 520 sends and receives data items from the network 526 via a wireless or wired transceiver 514. The transceiver 514 may be a cellular frequency, radio frequency (RF), infrared (IR) or any of a number of known wireless or wired transmission systems capable of communicating with a network 526 or other smart devices 102 having some or all of the features of the example computer of FIGS. 83 and 84. The bus 508 may represent one or more busses, e.g., USB, PCI, ISA (Industry Standard Architecture), X-Bus, EISA (Extended Industry Standard Architecture), or any other appropriate bus and/or bridge (also called a bus controller).

The computer 500 may be implemented using any suitable hardware and/or software, such as a personal computer or other electronic computing device. The computer 500 may be a portable computer, laptop, tablet or notebook computers, smart phones, PDAs, pocket computers, appliances, telephones, and mainframe computers are examples of other possible configurations of the computer 500. The network 526 may be any suitable network and may support any appropriate protocol suitable for communication to the computer 500. In an embodiment, the network 526 may support wireless communications. In another embodiment, the network 526 may support hard-wired communications, such as a telephone line or cable. In another embodiment, the network 526 may support the Ethernet IEEE (Institute of Electrical and Electronics Engineers) 802.3x specification. In another embodiment, the network 526 may be the Internet and may support IP (Internet Protocol). In another embodiment, the network 526 may be a LAN or a WAN. In another embodiment, the network 526 may be a hotspot service provider network. In another embodiment, the network 526 may be an intranet. In another embodiment, the network 526 may be a GPRS (General Packet Radio Service) network. In another embodiment, the network 526 may be any appropriate cellular data network or cell-based radio network technology. In another embodiment, the network 526 may be an IEEE 802.11 wireless network. In still another embodiment, the network 526 may be any suitable network or combination of networks. Although one network 526 is shown, in other embodiments any number of networks (of the same or different types) may be present.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or use the processes described in connection with the presently disclosed subject matter, e.g., through the use of an API, reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations. Although exemplary embodiments may refer to using aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be spread across a plurality of devices. Such devices might include personal computers, network servers, and handheld devices, for example.

Identification of Inhaler

The need to identify which inhaler, i.e. medicament container 28, is being used is important to providing objective, patient-specific adherence data since many patients have more than one inhaler, or medicament, that are to be used at different times or situations (e.g., rescue and/or controller medicaments). A common type of non-adherence is using a rescue inhaler regularly instead of a controller inhaler 28' because the rescue inhaler 28 provides immediate symptom relief. Without knowing which inhaler was used, health care providers cannot determine if the patient was adherent to the prescribed treatment protocol.

Figure 13:
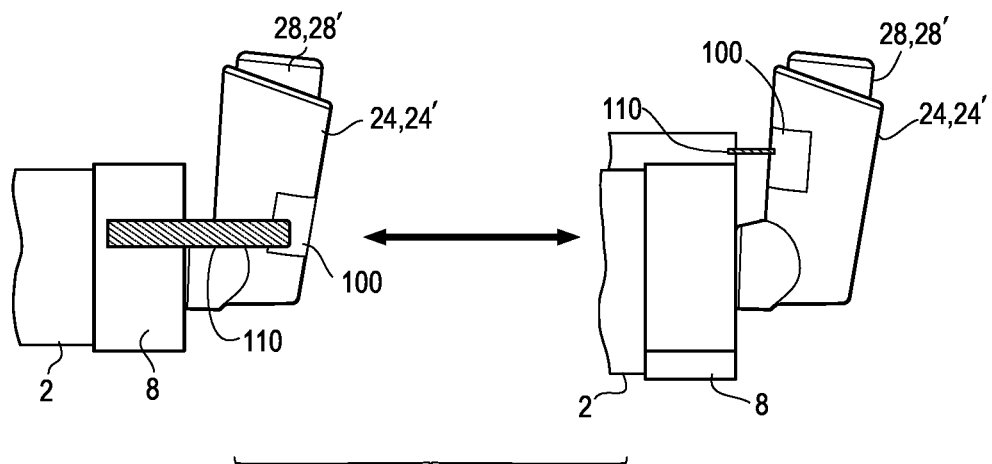
FIG. 13 are side views of embodiments of an MDI interfacing with a smart VHC.
Figure 14A:
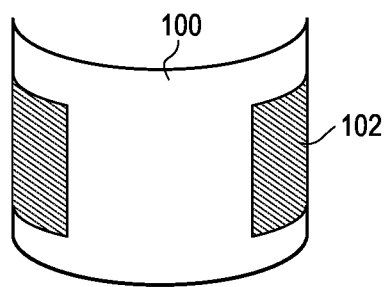
FIGS. 14A and B show front and rear views of an MDI identification label with embedded electrical contacts.
Figure 14B:
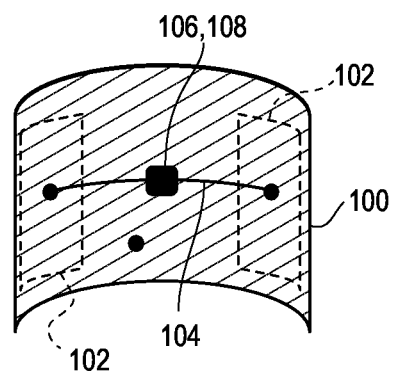

In one embodiment, and referring to FIGS. 13 and 14A and B, a passive electronic label 100 with a unique electrical characteristic (such as resistance, or serial number) is applied to the inhaler boot 26. The electrical characteristic is read, or recognized, each time the inhaler is actuated. The location(s) of the label 100 and contacts 102 applied thereto, shown in FIGS. 13 and 14, do not disrupt the drug delivery or airflow and allows the inhaler mouthpiece to be free of electronic components. The electronic label may be attached to the inhaler at the pharmacy by the pharmacist, or in the home by the patient or caregiver. In other embodiments, the electronic label could be embedded into the pharmacy label that is applied as the prescription is filled.

In one embodiment, shown in FIGS. 14A and B, two contact points 102 are provided on the front of the label, with the two contact points 102 being spaced far enough apart to prevent short-circuiting. The two contact points 102 are connected electrically with an electrical conductor 104, such as a wire, to an embedded passive electronic component 106 (i.e. resistor, capacitor, inductor), or an active electronic component 108 (i.e. memory chip, authentication chip, microprocessor, etc.). In an embodiment employing a resistor 106, the resistor may be in the range of 10Ω-10 MΩ. Implementing this embodiment with a simple series resistor circuit, a voltage divider, allows differentiation of inhalers by the resultant analog signal. For example, as shown in FIG. 13, a rescue inhaler 28 could have a 10Ω resistor and a controller inhaler 28' could have a 10 kΩ resistor. When attached to the smart VHC with one or more connectors 110 or contacts, the device will measure the resistance and then identify the inhaler as either a rescue or a controller inhaler 28, 28'. In the case that an EEPROM chip 108 is used, a unique serial ID will be assigned to each chip and upon first use, the user would enter their inhaler information into a companion app via smartphone or computer.

The backpiece 8, which is coupled to the input end of the holding chamber, has an electrical circuit and an opening. The mouthpiece 22 of the MDI, referred to as an insert portion, is moveable between an engaged position wherein the insert portion is received in the opening and a disengaged position wherein the insert portion is removed from the opening. The contacts 102 on the MDI, whether on a label 100 or accessory, complete the electrical circuit with one or more connectors 110 when the mouthpiece 22, or insert portion, is in the engaged position, whereinafter a circuit is complete and the identity of the MDI may be recorded and stored.

In another embodiment, shown in FIGS. 4A-11, a reusable identification accessory 120, 120', or adapter, may be applied to different inhalers, or moved from one inhaler to another, once the original inhaler expires or is emptied. The identification accessory 120, 120' includes a universal faceplate 122 and custom adapters 124, 124' to fit different boot shapes (see, e.g., FIGS. 4A-F).

Figure 11:
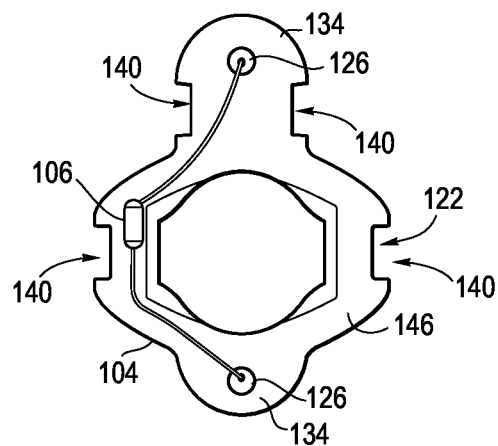
FIG. 11 is rear view of a MDI adapter face plate.

In one embodiment, the accessory uses magnets 126, which perform multiple roles: 1) the magnets support the physical weight of the inhaler while inserted into the smart VHC so that a reliable mechanical connection is maintained between the electrical contacts, 2) the magnets 126 form part of the electrical circuit by defining contacts 130, and 3) the magnets 126 ensure that the expelled drug output of the inhaler is aligned with the chamber body 2 so that the minimum amount of drug is deposited onto the chamber walls. It is possible to decouple the roles such that the magnets provide the inhaler support and positioning, while a separate pair of electrical contacts (e.g., as embedded in the label as described above or as positioned at different locations on the faceplate) complete the electrical circuit. FIG. 11 shows the rear view of the faceplate 122. In this embodiment, a resistor 106 is connected in series between two magnets 126 with an electrical conductor 104, such as a wire. When inserted into the smart VHC, the inhaler identification accessory, or magnets 126 on the face plate 120, 120', mates with two corresponding magnets 130 on the smart VHC as shown in FIGS. 7 and 8 and completes the circuit allowing the resistance value to be measured and the inhaler to be identified.

The face plate 122 includes a ring 146 having a central opening 132 shaped and dimensioned to receive the mouthpiece 22 of the inhaler therethrough, and a pair of lugs 134 extending upwardly and downwardly from the ring. The magnets are embedded in, or attached to, the lugs, such that a surface 136 of the magnets preferably extends rearwardly from the rear surface 138 of the face plate as shown in FIGS. 4A-F. The upper lug and opposite sides of the ring are configured with indentations, or notches 140, which are shaped to releasably engage resilient tabs 142 extending rearwardly from the adapter 124, 124'. It should be understood that the tabs may be disposed on the faceplate and engage notches on the adapter, or with configurations of both notches and tabs on each of the faceplate and adapter. In other embodiments, the adapter and faceplate may be releasably engaged through other mechanical connections, including without limitation, magnets, quick release fasteners, screws, detents, elastic bands, and combinations thereof. The magnets 134 are positioned on the upper and lower lugs, with the conductor 104 extending therebetween along a path defined by the ring 146 and with the resistor coupled to the ring 146.

As shown in FIGS. 4A-F and 10A-D, the adapter 124, 124' includes a mounting plate 147 having a downwardly facing yoke (inverted U-shape) having a mouth defining an opening 145 shaped to receive the mouthpiece of the inhaler therein, and a second mounting ring 148, 148', or retention member, extending rearwardly from the mounting plate 147. The second ring defines an axis extending transverse to an axis of the yoke opening, for example orthogonal thereto in one embodiment. The second ring is shaped and dimensioned to receive the chimney portion of the actuator boot and securely hold the MDI. The mounting plate 147, with its clips or tabs 142, is releasably secured to the face plate 122, with the location of the notches 140 ensuring proper alignment of the MDI relative to the face plate, and ultimately relative to the VHC. The mouthpiece 22 of the MDI is inserted through the backpiece 8 of the VHC, with the magnets 126, 130 engaging and ensuring proper alignment of the MDI in the VHC. At the same time, the interface between the magnets 126, 130 provides an electrical connection between the MDI and VHC, allowing the VHC to identify the MDI according to the measured resistance or unique serial identification.

Figure 21:
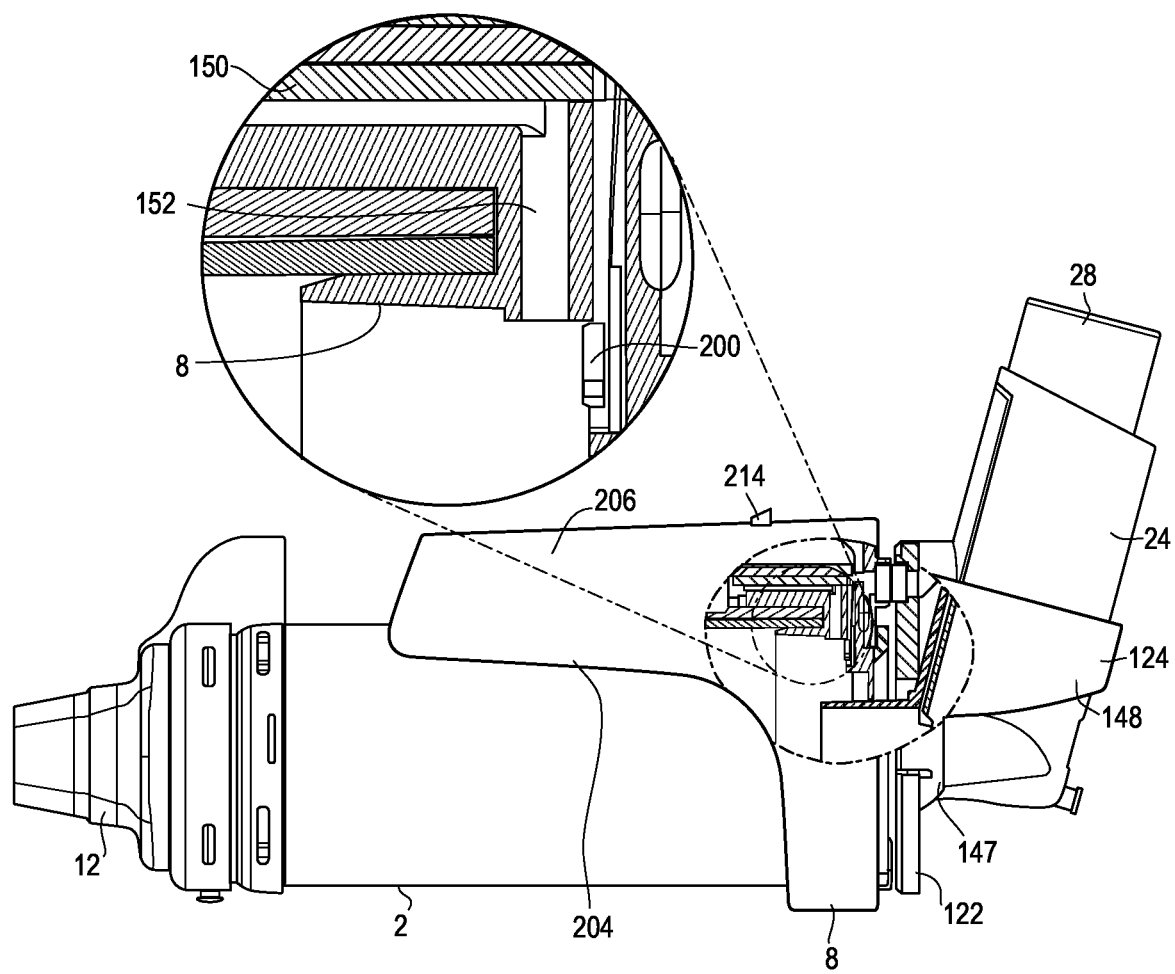
FIG. 21 is a side view of a smart VHC with a partial cut-away showing a microphone.

As shown in FIGS. 6 and 21, the backpiece 8 is outfitted with various electronic components. The backpiece includes an elastomeric ring component 202, which has a groove, and/or shoulder, shaped and dimensioned to receive the input end 10 of the holding chamber 2. The ring component has the pair of magnets 130 embedded therein. A shroud portion 204 extends forwardly from the ring component and at least partially surrounds the holding chamber. A housing 206 extends upwardly from the shroud and houses a USB charger 208, internal storage and/or processor 210, a battery 212 and/or MEMS flow sensor 150 therein. A microphone 200 may be coupled to, or embedded in, the ring component, for example proximate the interior space of the holding chamber to maximize audible readings of actuation. The magnets 130 are disposed in a circuit, which is closed by the magnets 126 on the MDI. One or more LED's 214 (e.g., array), or other indicators, are disposed on top of the housing and may provide feedback to the user, for example illuminating when one or more conditions are met, including for example one or more of a predetermined number of actuations have been competed, a predetermined number of breaths have been completed (e.g., sufficient to empty the holding chamber), a faulty valve is detected, and/or a need to clean the holding chamber is detected.

Figure 9A:
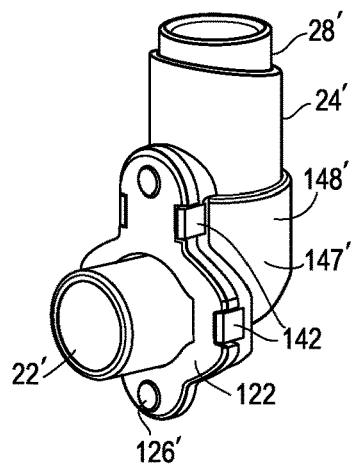
FIGS. 9A and B illustrate various MDI adapters coupled to different MDI's.
Figure 9B:
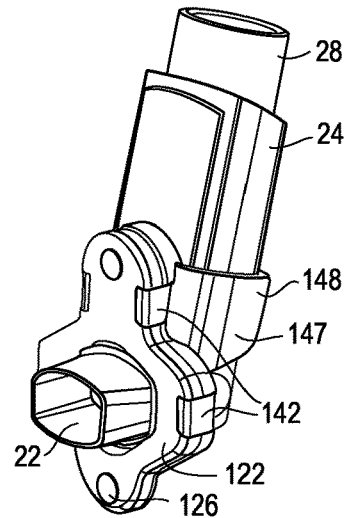
Figure 10A:
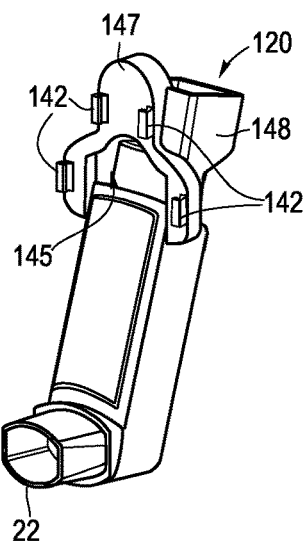
FIGS. 10A-D illustrate the assembly sequence of the MDI's and MDI adapters.
Figure 10B:
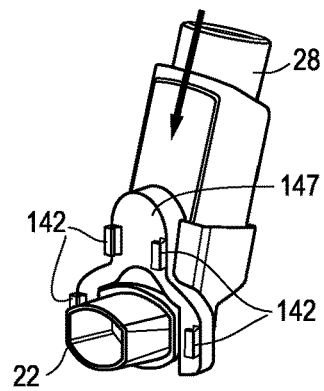
Figure 10C:
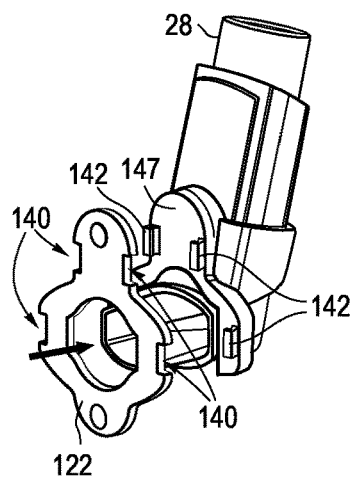
Figure 10D:
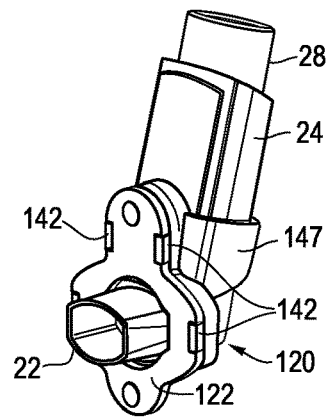

As shown in FIGS. 9A and B and 10A-D, the mounting plate 147 may be slid over the actuator boot 24 until the mouthpiece 22 is located in the opening 145 of the yoke. The face plate 122 is then slid over the mouthpiece 22 until the tabs 142 are engaged with the notches 140, thereby releasably securing the MDI to the faceplate 122, wherein after the adapter 120, 120' is ready to be secured to the VHC by way of the mouthpiece 22 being inserted into the backpiece 8 until the magnets 126, 130 are engaged.

Inhaler Actuation

One important aspect of a smart drug delivery device is the ability to identify when an inhaler has been actuated. The solution described herein makes use of a micro-electrical-mechanical-systems MEMS flow sensor 150 to detect the inhaler actuation, thereby reducing the number of sensors needed to perform both functions. Referring to FIGS. 6-8, one embodiment of the device is shown with some components removed for clarity. FIGS. 7 and 8 show the flow paths through the MEMS flow sensor for inspiratory and inhaler actuation, respectively. Exhalation is prevented from entering the chamber, and therefore the MEMS flow sensor 150, by the one-way inhalation valve 16 in the proximal part of the VHC.

Figure 12:
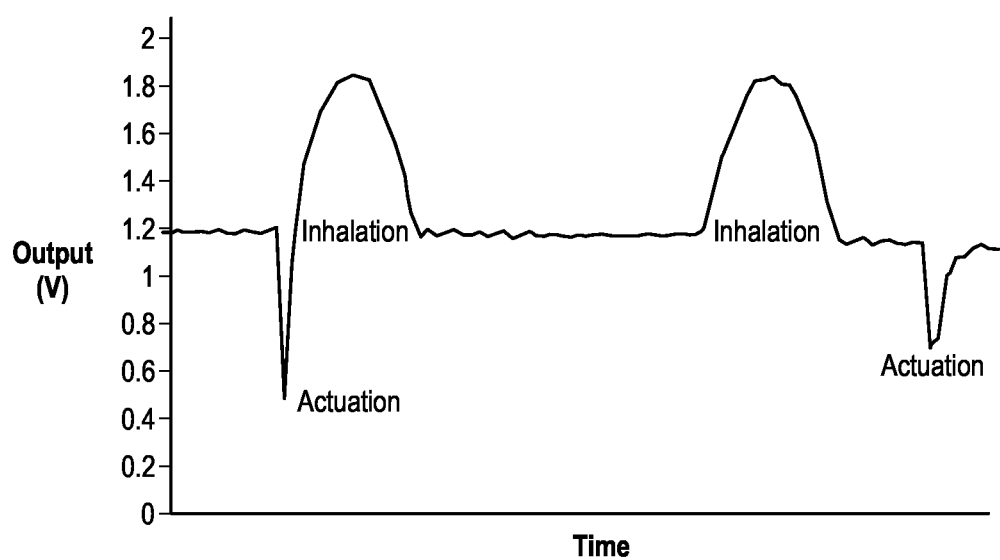
FIG. 12 is a graph showing output (Voltage) v. time during inhalation and actuation.

As the user begins to inhale, a negative pressure is created in the interior 4 of the chamber 2. This negative pressure draws air past the MEMS flow sensor 150 through a channel 152 molded into the inhaler backpiece. An example of the data recorded using a MEMS flow sensor is shown in FIG. 12. When the inhaler is actuated (FIG. 8), a positive pressure is created inside the chamber 2, 4 and air is pushed past the MEMS flow sensor 150 in the opposite direction. This reversed flow is detected as an inhaler actuation. Referring to FIG. 12, the gradual upward portions of the output indicate inhalation, while the sharp downwards portions indicate an actuation.

Faulty Valve Detection

Figure 15:
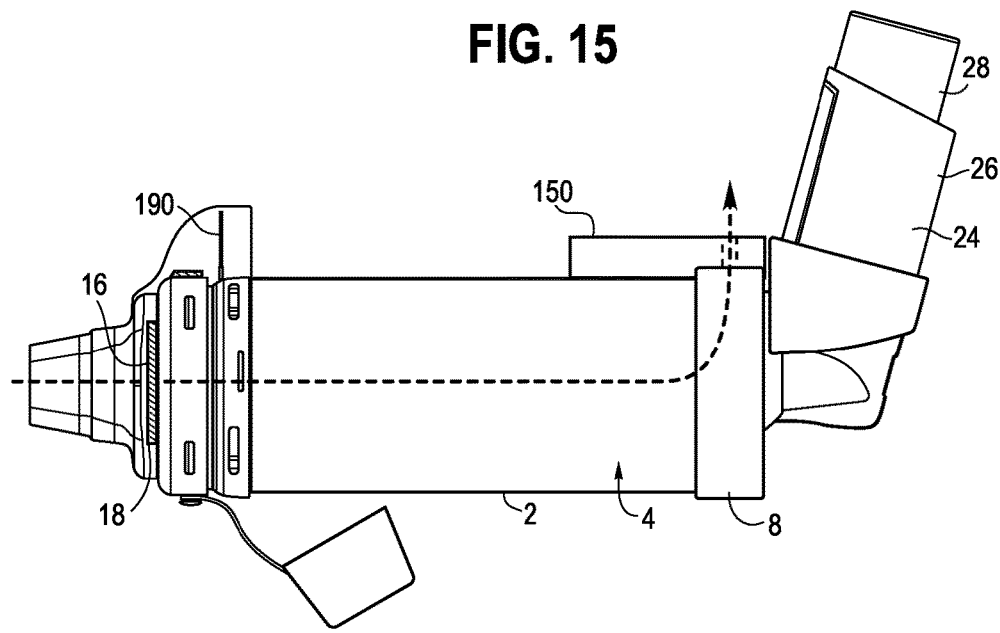
FIG. 15 is a side view schematic of a smart VHC illustrating an expiratory flow path with a faulty one-way valve.

In one embodiment, as shown in FIG. 15, the MEMS flow sensor 150 may also be used to provide indication of a faulty delivery device, for example a faulty valve 16. Under normal use, the patient's expiratory airflow is exhausted away from the device by way of the one-way valve 16 in the mouthpiece configured such that expired air does not enter the holding chamber. If the one-way valve 16 becomes dislodged, torn, or stuck open, expiratory air may enter the interior 4 of the holding chamber 2, thereby increasing the dead space of the device and expelling any remaining medicament from the chamber. In this situation, the MEMS flow sensor 150 will detect the expiratory airflow and the device will indicate that the valve may be malfunctioning and should be replaced. An algorithm distinguishes between an actuation (which produces a short and sharp spike) and expiratory airflow (which produces a longer and more gradual curve).

Cleaning Detection and Plume Analysis

Figure 16:
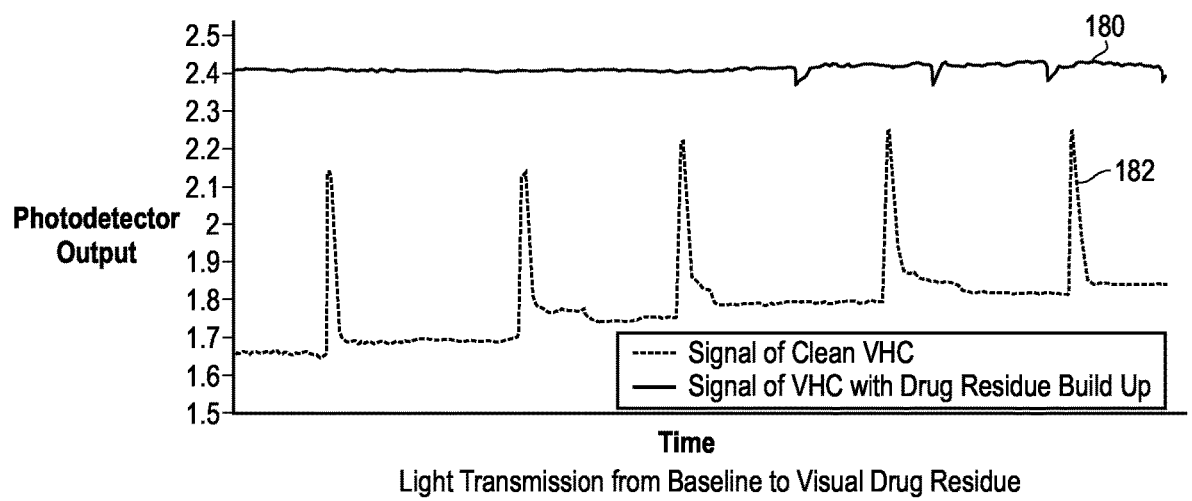
FIG. 16 is a graph showing photodetector output v. time for a clean VHC and a VHC with a build-up of drug residue.
Figure 17A:
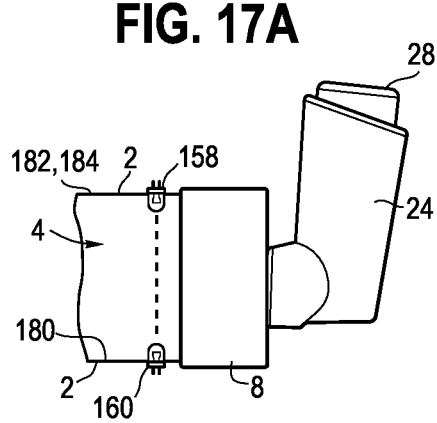
FIGS. 17A-C are partial views of smart VHC's with different light detection locations.
Figure 17B:
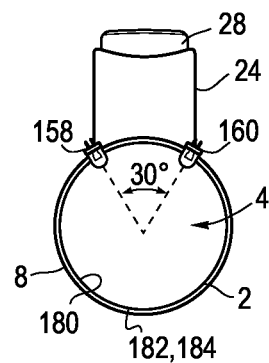
Figure 17C:
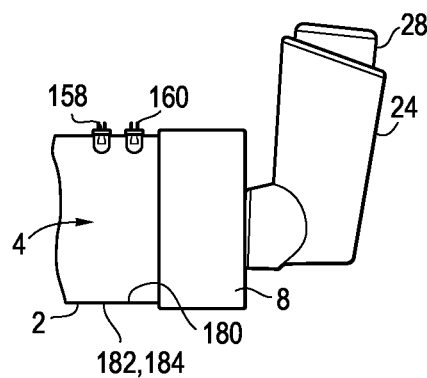

In one embodiment, and referring to FIGS. 16 and 17A-C, inhaler actuations may be detected by measuring the light reflected, transmitted, or blocked by the plume of the inhaler. Light detection technology may be used to provide the user with feedback such as when to clean or replace their device. In one embodiment, a baseline level of light transmission is set when the chamber is new or just cleaned. With each actuation, drug residue builds and coats the inside of the holding chamber reducing the amount of light that is transmitted by a transmitter (e.g., LED 158) and detected by the photodetector 160. A significant change in the detected light and therefore output signal of a photodetector 160 from the baseline state would indicate that the chamber needs to be cleaned or replaced if cleaning is not sufficient to remove residue. FIG. 16 shows baseline measurements of the light transmission via the photodetector signal for a new/clean device (182) compared to a device with visible drug build up within the chamber (180).

In one embodiment, the cleanliness of the chamber is determined by comparing the output of a first sensor 150 configured to detect inhaler actuation (like the MEMS flow sensor described above) to the output of a photodetector 160 also configured to detect inhaler actuation. If the first sensor 150 detects an actuation but the photodetector 160 does not detect an actuation (either by reflection, transmission, or reduction in light) it can be concluded that the interior of the chamber is not clean.

To improve light detection capabilities, a reflective surface 180, 182 (e.g., film) may be applied to the inside of, or wrapped around the exterior of, the valved holding chamber 2, such that the signal observed by the photodetector 160 for actuation detection or other purpose (see above) is amplified. The reflective surface faces radially inwardly toward the center of the interior of the holding chamber. The degree to which change in received light is observed by the photodetector is greater with a reflective surface for the light particles to reflect off. This surface coating 180, 182 will improve the reliability of actuation detection using light detection technology. Effective reflective surface coatings may include, aluminum foil, Mylar plastic, reflective paint, or aluminum applied to the exterior surface of the VHC or to the interior surface of a VHC covering.

At the same time, it is helpful to minimize the effects of ambient light. To minimize the effects of ambient light on the photodetector used for actuation or other purpose (see above), the smart valved holding chamber may be covered by an exterior overlay 184. Using a dark or light absorbent material, such as Vantablack, would eliminate virtually all sources of light outside of the chamber housing. The detection of aerosol particles scattering and reflecting the light within the chamber body is more reliable when isolated from exterior changes.

A secondary method for reducing the interference of ambient light is through modulation of a light source, and decoding the signal received by the photodetector 160. By emitting light using pulse width modulation of the forward current powering a LED 158 at a known frequency, the signal received by the photodetector 160 may be demodulated at this frequency to ignore artifacts. By subtracting the input signals from occurrences that the LED is on and off can effectively disregard noise produced by ambient light. This technique provides a more accurate detection of light scattering and reflection from aerosol particles and identification of an MDI actuation event.

In one embodiment, a first configuration (FIG. 17A), locates the LED 158 and photodetector 160 directly across the chamber from one another. In this position, the photodetector will see a decrease in the amount of received light as the aerosol plume blocks the direct line of sight to the LED.

In a second configuration (FIG. 17B), the LED 158 and photodetector 160 are positioned each 15 degrees offset from center at the top of the chamber. In this arrangement the two components should be located towards the front of the chamber body to detect scattering and reflection of the aerosol particles as the plume disperses. Suitable acute angles (e.g., between 0 and 180) greater than or less than 30 degrees would also work.

In a third configuration (FIG. 17C), the components are positioned adjacent to one another at the rear of the valved holding chamber body. This set up may also be placed on the bottom side of the chamber to detect a change in light due to the aerosol particles.

Proper Technique

Figure 18:
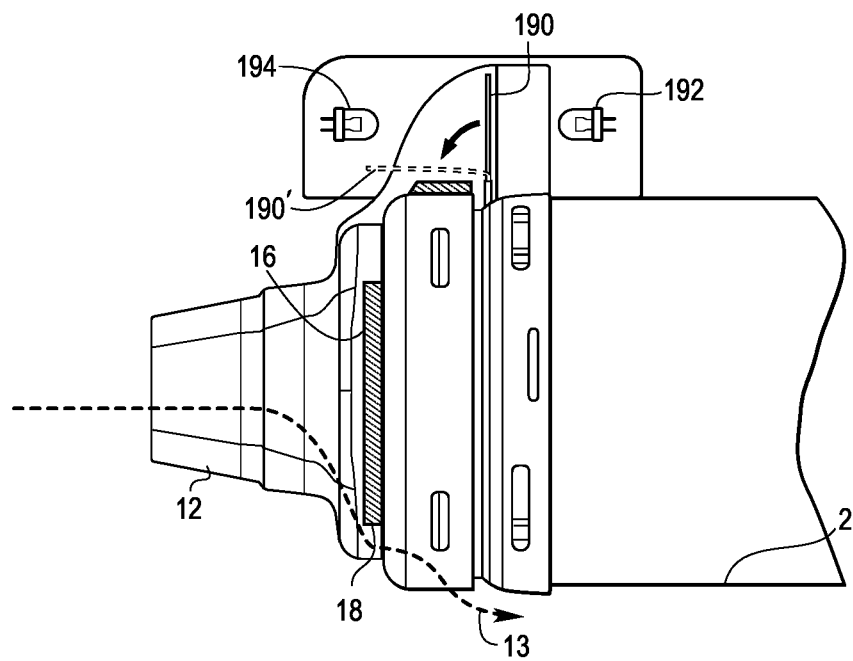
FIG. 18 is a partial side view of a smart VHC with a light curtain.

An important aspect in assessing therapy adherence is inhaler technique, which includes the user's inhalation characteristics. In one embodiment, and referring to FIG. 18, movement of a flow indicator 190 on the valved holding chamber indicates inhalation of the aerosol medication through the mouthpiece. The flow indicator 190 moves while there is flow through the chamber (by way of inhalation, exhalation and/or both) and returns to its static position during periods of no flow. Using an LED 194 and photodiode 192 as shown in FIG. 18, the photodiode 192 will receive light from the LED 194, or other transmission source, during inhalation while the flow indicator 190' is down. When inhalation stops the flow indicator 190 returns to an upright position and blocks the photodiode from observing the LED. Detecting this binary output (open or closed) will identify the length of user's inhalation and the number of breathes taken for each inhaler actuation. Patient behavior and technique can be inferred from this recorded data. This configuration, including LED and photodiode, may be contained within a housing to isolate the components from ambient light. It should be understood that the viewing port 198, in which the flow indicator moves, may be blacked out.

Smart VHC Components

In one embodiment, and referring to FIGS. 1-3C, 6 and 19, a smart valved holding chamber (VHC) includes a valved holding chamber 2, an electronic backpiece 8 and an inhaler, or MDI, with an identification accessory 120. The three main features of the smart VHC are to detect and record the date, time and identification of each inhaler actuation, to record the inhalation characteristics to reach actuation and to provide feedback on proper technique.

In the preferred embodiment, shown in FIGS. 6 and 21, actuation detection will be performed by a MEMS flow sensor 150 with a MEMS microphone 200 as a backup. As discussed previously, a bypass channel 152 extends from atmosphere through to the chamber's interior. Upon actuation of an inhaler, a pressure differential between the atmospheric and interior openings of the channel 152 is created, causing a small negative flow past the sensor 150 to atmosphere. Detection of this rapid negative flow profile indicates the actuation of an inhaler.

When an inhaler is actuated during inhalation, the negative pressure from the inhalation may cancel out the positive pressure from the inhaler actuation in which case the MEMS flow sensor 150 cannot reliably determine if an inhaler was actuated. In this case, a MEMS microphone 200 is used to identify sounds indicative of an inhaler actuation. The microphone 200 is housed in the holding chamber backpiece 8 near the inhaler mouthpiece and is used to identify inhaler actuations when the MEMS flow sensor 150 detects inhalation flow.

Figure 20:
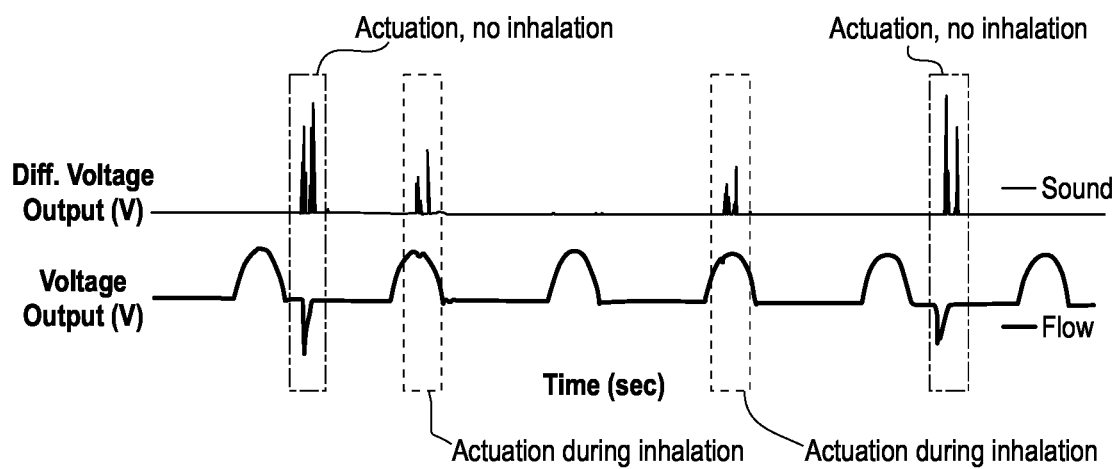
FIG. 20 is a graph showing voltage output from a flow sensor and microphone showing actuation and inhalation.

FIG. 20 shows the voltage output from the MEMS flow sensor 150 and the microphone 200 during several inhaler actuations and inhalation cycles. When inhalation is not occurring, the MEMS flow sensor 150 can reliably determine if an inhaler has been actuated. However, during inhalation the negative flow from the release of pressurized medication and propellant is not reliably distinguishable, unless the output from the microphone is considered.

FIG. 6 shows the location and geometry of the MEMS flow sensor, the backpiece, the bypass flow channel contained within the backpiece 8, and the MEMS microphone 200. The method to identify which inhaler is inserted into the smart VHC relies on measuring the electrical characteristics of an accessory which is added to each inhaler prescribed for the user. Varying the electrical characteristics of each inhaler accessory is performed by varying the embedded resistor 106 connected to each embedded magnet 126. A universal faceplate 122 that can be attached to most inhalers contains the embedded magnets and resistor. Unique adapters that accommodate the different inhaler shapes and styles are also available. As shown above in FIGS. 4A-F, the unique adapter is positioned over the inhaler boot, and the universal faceplate is attached over the mouthpiece of the inhaler.

In the preferred embodiment, a MEMS flow sensor 150 is used to record inhalation flow data to determine if proper technique was achieved. Examples of the output from the MEMS flow sensor is shown in FIG. 20. By analyzing the actuation and inhalation data collected by the sensor, feedback is given to the patient, caregiver, or physician about errors in the user's technique that are critical to proper use of an inhaler with spacer.

Examples of the types of technique errors that can be detected include:

| | Technique Error | Detection Method |
|---|---|---|
| 1 | Failure to properly align the inhaler within the spacer (i.e. inhaler mouthpiece is angled upwards or downwards). | The magnetic attachment system prevents misalignment and signals that an inhaler is present and installed correctly. |
| 2 | Failure to ensure a tight seal when the inhaler is inserted into spacer. | The magnetic attachment system prevents misalignment and the flexible backpiece ensures a tight seal |
| 3 | Failure to hold spacer with inhaler upright | Two opposite facing tilt sensors on the sVHC's circuit board are used to detect if the chamber is tilted >30° from horizontal |
| 4 | Failure to actuate just one dose into chamber | TRUE if multiple actuations are detected within a specified timeframe (e.g. 5 secs) |
| 5 | Failure to actuate a dose into chamber | TRUE if an inhaler is attached and multiple inhalations have been detected, but no actuations |
| 6 | Failure to inhale through chamber within 2 seconds of actuation | TRUE if inhalation does not begin within 2 seconds, OR has not already started |
| 7 | Failure to inhale through chamber (i.e. inhales through nose) | TRUE if actuations are detected but not inhalation |
| 8 | Failure to inhale slow and deep | TRUE if inhalation flow rate OR breath rate exceeds a specified value |
| 9 | Failure to hold breath | TRUE if breath rate exceeds a specified value |

Figure 19:
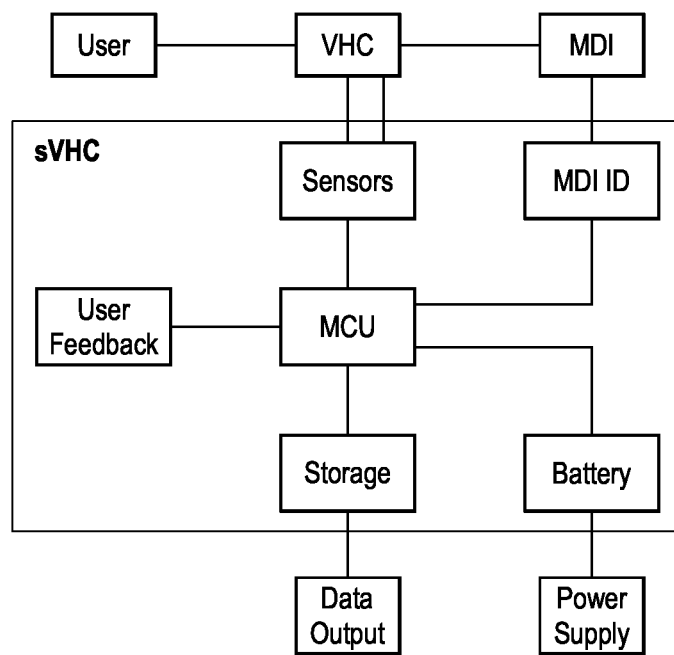
FIG. 19 is a block diagram of a system architecture for a smart VHC.

The recorded date, time and identification of each inhaler actuation, as well as the inhalation data, are stored in on-board memory. Data will be delivered to the user's phone or computer for analysis via wireless (BTLE) or wired (USB) methods as shown in FIG. 19. If paired with a previously synced device, usage data will be transferred in real-time. If no device is detected, the data will be stored on-board and history will be transferred during the next connection.

Feedback may be provided to the user in real-time to confirm proper use of the smart VHC.

Providing feedback to users regarding their inhalation technique is one feature of the VHC that will help optimize drug delivery. In one embodiment, the flow sensor 150 may be used to collect data and provide feedback about technique. The flow sensor measures the flow rate at which the user is inhaling. Inhaling too fast may deposit most of the drug in the throat rather than in the lungs. Effective drug deposition into the lungs may be achieved with controlled inhalation. In addition, the flow rate may be integrated over time to determine the volume of air inhaled, which may be used to provide the user with an indication of when they have emptied the interior space of the chamber housing and received a complete dose. The flow rate information may be used in real-time to provide feedback to the user about practice sessions, for example through a feedback device such as an indicator (visual, auditory and/or haptic) or display, and whether they should begin inhalation, and/or whether they need to slow down the flow rate, for example when exceeding a maximum flow rate. MDI actuation may also be used to provide feedback to the user about initiating actuation and/or beginning inhalation.

As shown in FIG. 19, a controller, which may be located on or inside the various embodiments of the smart VHC described herein, is in communication with one or more sensors, switches and or gauges that are tracking or controlling operation of the smart VHC. The controller may store data gathered in a memory for later download to a receiving device, or may transmit data to a receiving device in real-time. Additionally, the controller may perform some processing of the gathered data from the sensors, or it may store and transmit raw data. RF transmitter and/or receiver modules may be associated with the controller on the smart VHC to communicate with remote hand-held or fixed computing devices in real-time or at a later time when the smart VHC is in communication range of a communication network to the remote hand-held or fixed location computing devices. The controller may include one or more of the features of the computer system 500 shown in FIG. 22. Additionally, the one or more sensors, switches or gauges may be in wired or wireless communication with the controller.

For clarity in displaying other features of the various Smart VHC embodiments described, the controller circuitry is omitted, however a controller or other processing agent capable of at least managing the routing or storing of data from the smart VHC is contemplated in one version of these embodiments. In other implementations, the smart VHC may not include an onboard processor and the various sensors, gauges and switches of a particular embodiment may wirelessly communicate directly with a remotely located controller or other processing device, such as a handheld device or remote server. Data gathered by a controller or other processing device may be compared to expected or pre-programmed values in the local controller memory or other remote location to provide the basis for feedback on whether desired performance or therapy is taking place. If the controller is a more sophisticated and includes more of the computer 500 elements shown in FIG. 22, then this processing may all be local to the smart device (smart VHC, smart MDI, etc.). In more rudimentary controller arrangements, the data may simply be date/time stamped and stored locally or remotely for later processing. In one embodiment, the data may further be locally or remotely stamped with a unique device or patient identifier.

The MDI may be configured with a dose counter module, which has been actuated for the purpose of adherence monitoring and captures dose actuation time, count and total. At the same time, the VHC may be configured with a flow detection module, which captures inhalation time, duration and count, with the modules being in communication, for example with Bluetooth technology. Communications with these devices from the smart VHC or its application can be used to detect and confirm MDI actuation and technique.

In any of the above-described embodiments of smart devices, the controller or other processing element that communicates with or controls the sensors, gauges or switches may be integrated into, positioned on or in, or remotely located from the smart device itself. It should be understood that the various sensors, gauges or switches may serve multiple functions and may be used in various combinations, all in communication with the controller or other processing element. Additionally, for any of the smart devices described above, some or all of the data gathered and feedback provided to a user of the device by sensors, switches or gauges may simultaneously be transmitted to a remotely located caregiver. The remotely located caregiver or monitoring agency may intervene to provide further advice or information during a therapy session. Alternatively, the data and feedback transmitted to the caregiver or monitoring agency in parallel with the user may be stored remotely for later assessment by medical professionals. Concurrent transmission to a remote source of information, including the sensed data and any feedback, may also prevent problems with tampering or corruption of data stored on the smart device itself.

The battery or other power supply for any controller circuitry, sensors, gauges and switches may be rechargeable or removable in different embodiments of smart devices described herein. In order to minimize battery drain, certain of the sensors may be configured for a predetermined sampling frequency rather than a continuous measurement mode. Also, the circuitry on the smart device may only activate upon the detection of a particular event and may automatically turn off after a predetermined period from the initial trigger or after sensed idle period for the device.

Although the present invention has been described with reference to preferred embodiments. Those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. An identification accessory for coupling an MDI to a holding chamber comprising:
   a faceplate having an opening shaped to receive an insert portion of the MDI, wherein the faceplate comprises a pair of spaced apart magnets electrically connected to a passive and/or active electronic component, and wherein the magnets are adapted to engage a backpiece component of the holding chamber; and
   an adapter releasably coupled to the faceplate, the adapter comprising a retention member shaped to engage the MDI.

2. The identification accessory of claim 1 wherein the opening comprises a first opening, and wherein the adapter comprises a U-shaped yoke defining a second opening aligned with the first opening.

3. The identification accessory of claim 2 wherein the second opening of the yoke comprises a downwardly opening mouth.

4. The identification accessory of claim 2 wherein the second opening defines a first axis, and wherein the adapter further comprises a ring shaped and configured to receive a chimney portion of the MDI, wherein the ring defines a second axis extending transverse to the first axis.

5. The identification accessory of claim 1 wherein one of the adapter and/or faceplate comprises one or more tabs releasably engaged with notches on the other of the adapter and/or faceplate.

6. The identification accessory of claim 1 wherein the magnets define spaced apart electrical contacts.

7. The identification accessory of claim 1 wherein the faceplate comprises a first pair of spaced apart electrical contacts.

8. An identification accessory for coupling an MDI to a holding chamber comprising:
   a faceplate having an opening shaped to receive an insert portion of the MDI, wherein the faceplate comprises a pair of spaced apart magnets electrically connected to a passive and/or active electronic component, wherein the passive electronic component comprises a resistor; and an adapter releasably coupled to the faceplate, the adapter comprising a retention member shaped to engage the MDI.

9. An identification accessory for coupling an MDI to a holding chamber comprising:
a faceplate having an opening shaped to receive an insert portion of the MDI, wherein the faceplate comprises a first pair of spaced apart electrical contacts; and
an adapter releasably coupled to the faceplate, the adapter comprising a retention member shaped to engage the MDI; and
a backpiece configured to be coupled to the holding chamber, wherein the backpiece comprises an electrical circuit, a second pair of spaced apart electrical contacts and an opening shaped to receive the insert portion of the MDI, wherein the first and second pairs of electrical contacts are moveable between a disengaged position and an engaged position, wherein the first and second pairs of electrical contacts complete the electrical circuit when moved to the engaged position.

10. The identification accessory of claim 9 wherein at least one of the first and second pair of contacts comprises a pair of magnets, and wherein the faceplate is magnetically coupled to the backpiece when the first and second pairs of electrical contacts are moved to the engaged position.

11. The identification accessory of claim 9 wherein the backpiece comprises a ring component shaped and dimensioned to receive an input end of the holding chamber.

12. The identification accessory of claim 11 wherein the backpiece further comprises a shroud portion extending forwardly from the ring component.

13. The identification accessory of claim 11 wherein the backpiece comprises a microphone coupled to the ring component.

14. The identification accessory of claim 9 wherein the backpiece comprises a housing.

15. The identification accessory of claim 14 further comprising a USB charger, an internal storage, a processor, a battery and/or a flow sensor disposed in the housing.

16. The identification accessory of claim 9 wherein the backpiece comprises a visual indicator adapted to provide feedback to a user.

* * * * *